(12) United States Patent
Weinberg

(10) Patent No.: US 7,442,375 B2
(45) Date of Patent: Oct. 28, 2008

(54) COMPOSITIONS OF BETA-DEFENSIN INDUCING AGENTS

(75) Inventor: Aaron Weinberg, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 10/891,825

(22) Filed: Jul. 14, 2004

(65) Prior Publication Data

US 2005/0075292 A1 Apr. 7, 2005

Related U.S. Application Data

(63) Continuation-in-part of application No. 10/737,288, filed on Dec. 15, 2003, now abandoned.

(60) Provisional application No. 60/433,099, filed on Dec. 13, 2002.

(51) Int. Cl.
*A61K 39/00* (2006.01)
*A61K 39/02* (2006.01)
*C07K 1/00* (2006.01)

(52) U.S. Cl. .................. 424/185.1; 424/190.1; 530/350
(58) Field of Classification Search .............. 424/184.1; 435/5

See application file for complete search history.

(56) References Cited

U.S. PATENT DOCUMENTS 5,756,666 A * 5/1998 Takiguchi et al. ........... 530/327

FOREIGN PATENT DOCUMENTS

| JP | 2002186485 | 7/2002 |
| WO | WO-99/64439 | 12/1999 |
| WO | WO-01/38349 | 5/2001 |
| WO | WO-02/22686 | 3/2002 |
| WO | WO-02/064154 | 8/2002 |

OTHER PUBLICATIONS

Bonvissuto, K. The Natural. CWRU Magazine, Spring 2002, p. 26-29. [retrieved on Aug. 2, 2006]. Retrieved from the Internet <URL:www.cwru.edu/pubs/cwrumag/spring2002/features/natural/download/Natural.pdf>.*
Tuner et al. Purification and Propertiesof a Novel P-Lactamase from Fusobacterium necleatum. Antimicrobial Agents and Chemotherapy, Jun. 1985, vol. 27, No. 6, p. 943-947.*
Kaur et al. Characterization of shared antigens of Fusobacterium nucleatum and Fusobacterium necrophorum. Oral Microbiology and Immunology Oct. 1992, vol. 7, No. 5, p. 291-298.*
Mineyama et al. Some properties of gamma-glutamyl transpeptidase from Fusobacterium nucleatum. Microbios 1997, vol. 90, No. 364-365, p. 187-200.*
Krisanaprakornkit et al. Inducible Expression of Human b-Defensin 2 by Fusobacterium nucleatum in Oral Epithelial Cells: Multiple Signaling Pathways and Role of Commensal Bacteria in Innate Immunity and the Epithelial Barrier. Infection and Immunity, May 2000, vol. 68, No. 5, p. 2907-2915.*
Harder et al., "Isolation and characterization of human beta-defensin-3, a novel human inducible peptide antibiotic," Journal of Biological Chemistry, American Society of Biological Chemists 276(8):5707-5713 (2001).
Kapatral et al., "Genome sequence and analysis of the oral bacterium Fusobacterium nucleatum strain ATCC 25586," J. Bacteriol 184(7): 2005-2018 (2002).

* cited by examiner

*Primary Examiner*—Bruce Campell
*Assistant Examiner*—Louise Humphrey
(74) *Attorney, Agent, or Firm*—Hahn Loeser & Parks LLP; John J. Cunniff

(57) ABSTRACT

The disclosure provides, among other things, beta-defensin related agents for the treatment and prevention of viral infections, and particularly HIV infections. The disclosure provides methods for identifying additional beta-defensin related agents and for improving available beta-defensin related agents.

7 Claims, 6 Drawing Sheets

NHOECs challenged with HIV R5 or X4; 24 or 48 hrs

```
SEQUENCE LISTING

<160> NUMBER OF SEQ ID NOS: 21

<210> SEQ ID NO 1
<211> LENGTH: 41
<212> TYPE: PRT
<213> ORGANISM: Homo sapiens

<400> SEQUENCE: 1

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40

<210> SEQ ID NO 2
<211> LENGTH: 64
<212> TYPE: PRT
<213> ORGANISM: Homo sapiens

<400> SEQUENCE: 2

Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 3
```

<211> LENGTH: 121
<212> TYPE: PRT
<213> ORGANISM: Fusobacterium nucleatum

<400> SEQUENCE: 3

```
Met Ser Leu Phe Leu Val Ala Cys Gly Glu Lys Lys Glu Glu Lys
 1               5                  10                  15

Pro Ala Glu Gln Ala Ala Val Glu Ala Thr Ala Thr Glu Ala Pro Ala
             20                  25                  30

Thr Glu Thr Thr Glu Ala Ala Ala Glu Ala Lys Thr Phe Ser Leu Lys
         35                  40                  45

Thr Glu Asp Gly Lys Glu Phe Thr Leu Val Val Ala Ala Asp Gly Ser
     50                  55                  60

Thr Ala Thr Leu Thr Asp Ala Glu Gly Lys Ala Thr Glu Leu Lys Asn
 65                  70                  75                  80

Ala Glu Thr Ala Ser Gly Glu Arg Tyr Ala Asp Glu Ala Gly Asn Glu
                 85                  90                  95

Val Ala Met Lys Gly Ala Glu Gly Ile Leu Thr Leu Gly Asp Leu Lys
            100                 105                 110

Glu Val Pro Val Thr Val Glu Ala Lys
        115                 120
```

<210> SEQ ID NO 4
<211> LENGTH: 2045
<212> TYPE: DNA
<213> ORGANISM: Homo sapiens

<400> SEQUENCE: 4

| | | | | | |
|---|---|---|---|---|---|
| ctttataagg | tggaaggctt | gatgtcctcc | ccagactcag | ctcctggtga | agctcccagc | 60 |
| catcagccat | gagggtcttg | tatctcctct | tctcgttcct | cttcatattc | ctgatgcctc | 120 |
| ttccaggtga | gatgggccag | ggaaatagga | gggttggcca | atggaagaa | tggcgtagaa | 180 |
| gttctctgtc | tcctctcatt | cccctccacc | tatctctccc | tcatccctct | ctctccttcc | 240 |
| tctctctgtg | tgtcccctcc | atcctttct | cctgcttctc | tctcttcttc | cctctctctc | 300 |
| tttttctgt | ctttctttt | cctctctccc | tagagcatgt | ctttctttct | ttctctttcc | 360 |
| tttcttctac | ccacactttt | agactgaatg | ccctatttaa | ttgaacaaag | cattgcttcc | 420 |
| ttcaatagaa | aaggagtttg | agaacccaat | ggacacctca | ctcgttcttc | taagccaata | 480 |
| tgaaggagcc | cagtagcttg | taaatatcat | ctcttcactg | ctttccatgc | tacaactgct | 540 |
| gagactatgg | ttgaaacctg | ttaggtgact | tttaaataa | aaggcagaaa | ttttgatttt | 600 |
| atctaaagaa | agtagtatag | aatgtcattt | tctaaatttt | tatatttaaa | gggtagatac | 660 |
| tgcaacctag | agaattccag | ataatcttaa | ggcccagcct | atactgtgag | aactactgca | 720 |
| gcaagacact | ctgcctccag | gacttttctg | atcagaggcc | ctgagaacag | tccctgccac | 780 |
| taggccactg | caggttcaca | ggacagggta | cagcccattg | aaacctactt | ttaaacctgg | 840 |
| atgcctaacc | ttcatttct | ccttgatatt | atgaaaataa | aataaaaacc | atgaaaggat | 900 |
| aaaagaggga | gagtggaagg | gaaggatgga | gaaagggaaa | agaaaattt | gagagtaaat | 960 |
| cctaaaacaa | ttaatctaat | agatatcatc | ttgtgaaatc | ctcattttac | caatcttatt | 1020 |
| tatgagtcct | gggttttgtg | agaacaatgg | ggttctgaga | ggcaccagag | acctcatgtt | 1080 |
| ttccaaaacc | tagaacagta | taatgaagga | aggcggggag | gcagggaggc | agggaggcag | 1140 |
| ggaggcaggg | aggcgggcag | gtggggaggg | agggacggaa | ggagggaggg | agggagggag | 1200 |
| ggagggaggg | agggataaaa | aaagaagaat | gaggttgaaa | ccaggactta | gatattagaa | 1260 |

```
acaagccatt acaaaattta tttctatggt taattgtggt tttcaactgt aagttacttg    1320
gtgttaattt cctattaaac aatttcagta agttgcatct ttttatccca tctcaggtca    1380
aatacttaac agactaaatg atttgaaaaa gcaaaagttt actggcttgt gtgtgttaaa    1440
atggaggtat ggtggctttg atattatctt cttgtggtgg agctgaattc acaagagatc    1500
gttgctgagc tcctaccaga ccccacctgg aggccccagt cactcaggag agatcagggt    1560 cttttcacaat caggttctac aaaaataaac atccccccaa ccacagcagt gccagtttcc    1620
atgtcagaaa cttagatcca aatgactgac tcgcgtctca ttatcatgat ggaaaagccc    1680
aggcttgaga agaagcccg ctgcggattt actcaaggcg atactgacac agggtttgtg    1740
tttttccaac atgagttttg agttcttaca cgctgtttgc tcttttttgtg tgttttttcc    1800 ctgttaggtg ttttttggtgg tataggcgat cctgttacct gccttaagag tggagccata    1860
tgtcatccag tcttttgccc tagaaggtat aaacaaattg gcacctgtgg tctccctgga    1920
acaaaatgct gcaaaaagcc atgaggaggc caagaagctg ctgtggctga tgcggattca    1980
gaaagggctc cctcatcaga gacgtgcgac atgtaaacca aattaaacta tggtgtccaa    2040
agata                                                                 2045

<210> SEQ ID NO 5
<211> LENGTH: 319
<212> TYPE: DNA
<213> ORGANISM: Homo sapiens

<400> SEQUENCE: 5
ggtgaagctc ccagccatca gccatgaggg tcttgtatct cctcttctcg ttcctcttca      60
tattcctgat gcctcttcca ggtgttttttg gtggtatagg cgatcctgtt acctgcctta    120
agagtggagc catatgtcat ccagtctttt gccctagaag gtataaacaa attggcacct    180
gtggtctccc tggaacaaaa tgctgcaaaa agccatgagg aggccaagaa gctgctgtgg    240
ctgatgcgga ttcagaaagg gctccctcat cagagacgtg cgacatgtaa accaaattaa    300
actatggtgt ccaaagata                                                   319

<210> SEQ ID NO 6
<211> LENGTH: 195
<212> TYPE: DNA
<213> ORGANISM: Homo sapiens

<400> SEQUENCE: 6
atgagggtct tgtatctcct cttctcgttc ctcttcatat tcctgatgcc tcttccaggt      60 gttttttggtg gtataggcga tcctgttacc tgccttaaga gtggagccat atgtcatcca    120
gtcttttgcc ctagaaggta taaacaaatt ggcacctgtg gtctccctgg aacaaaatgc    180
tgcaaaaagc catga                                                       195

<210> SEQ ID NO 7
<211> LENGTH: 126
<212> TYPE: DNA
<213> ORGANISM: Homo sapiens

<400> SEQUENCE: 7
ggtataggcg atcctgttac ctgccttaag agtggagcca tatgtcatcc agtcttttgc      60
cctagaaggt ataaacaaat tggcacctgt ggtctccctg gaacaaaatg ctgcaaaaag    120
ccatga                                                                 126
```

<210> SEQ ID NO 8
<211> LENGTH: 366
<212> TYPE: DNA
<213> ORGANISM: Homo sapiens

<400> SEQUENCE: 8

```
atgagtttat tcttagtagc ttgtggagaa aaaaagaag aagaaaaacc agctgaacaa      60
gctgctgtag aagcaactgc aactgaagca cctgctacag aaacaactga agctgctgct     120
gaagctaaaa cattctcact taaaactgaa gatggaaaag aattcacatt agtagttgct     180
gctgatggaa gtactgcaac tttaactgat gcagaaggaa agcaactga attaaaaaat      240
gctgaaactg catctggaga agatatgca gatgaagctg aaacgaagt tgctatgaaa       300
ggtgcagaag gaatcttaac tttaggagac cttaaagaag taccagtaac tgttgaagct     360
aaatag                                                                366
```

<210> SEQ ID NO 9
<211> LENGTH: 129
<212> TYPE: PRT
<213> ORGANISM: Fusobacterium nucleatum

<400> SEQUENCE: 9

```
Met Lys Lys Ile Leu Leu Leu Ser Ser Leu Phe Leu Phe Ala Cys
 1               5                  10                  15

Ala Asn Ile Asp Thr Gly Val Asp Glu Ser Lys Glu Ala Gln Ile Ser
                20                  25                  30

Arg Leu Leu Lys Glu Ala Asp Lys Lys Glu Lys Thr Val Glu Val
         35                  40                  45

Glu Lys Lys Leu Val Thr Asp Asn Gly Glu Val Ile Glu Glu
 50                  55                  60

Ala Thr Val Gln Asn Lys Lys Ser His Lys Gly Met Thr Arg Gly Glu
 65                  70                  75                  80

Ile Met Glu Tyr Glu Met Thr Arg Val Ser Asp Glu Met Asn Ala Leu
                85                  90                  95

Gln Ala Asp Val Gln Gln Tyr Gln Glu Lys Lys Ala Gln Leu Lys Ala
                100                 105                 110

Tyr Gln Glu Lys Leu Gln Lys Leu Glu Glu Leu Asn Asn Ala Gly Ile
        115                 120                 125

Lys
```

<210> SEQ ID NO 10
<211> LENGTH: 390
<212> TYPE: DNA
<213> ORGANISM: Fusobacterium nucleatum

<400> SEQUENCE: 10

```
ttgaaaaaaa tattattact attatcttct ttatttttat ttgcttgtgc taatatagat      60
acaggtgtag atgaaagtaa agaagctcaa atatcaagac ttttaaaaga agctgataag     120
aaaaaagaaa aaacagtaga agtagaaaag aaacttgtaa ctgataatgg agaggaagtt     180
atagaggaag aagctaccgt tcaaaacaaa aaatcacata aggaatgac aagagggaa       240
ataatggaat atgaaatgac aagagtttca gatgaaatga atgccctaca agcgatgta     300
caacaatatc aagaaagaa agcacaacta aaagcatacc aagaaaaatt acaaaaatta     360
gaagaattaa ataatgcagg aataaaataa                                     390
```

<210> SEQ ID NO 11
<211> LENGTH: 123
<212> TYPE: PRT
<213> ORGANISM: Fusobacterium nucleatum

<400> SEQUENCE: 11

Met Lys Lys Val Ile Leu Thr Leu Phe Val Leu Leu Ser Ile Gly Ile
1               5                   10                  15

Phe Ala Asn Asp Glu Ile Ile Ser Glu Leu Lys Gly Leu Asn Ala Glu
            20                  25                  30

Tyr Glu Asn Leu Val Lys Glu Glu Ala Arg Phe Gln Lys Glu Lys
        35                  40                  45

Glu Leu Ser Glu Arg Ala Ala Ala Gln Asn Val Lys Leu Ala Glu Leu
    50                  55                  60

Lys Ala Ser Ile Glu Glu Lys Leu Leu Ala Ala Pro Glu Glu Arg Lys
65                  70                  75                  80

Thr Lys Phe Phe Lys Asp Thr Phe Asp Gly Leu Val Lys Asp Tyr Ser
                85                  90                  95

Lys Tyr Leu Ser Gln Ile Asn Glu Lys Ile Ala Glu Asn Thr Glu Ile
            100                 105                 110

Val Ser Asn Phe Glu Lys Ile Gln Lys Ile Arg
        115                 120

<210> SEQ ID NO 12
<211> LENGTH: 372
<212> TYPE: DNA
<213> ORGANISM: Fusobacterium nucleatum

<400> SEQUENCE: 12
atgaaaaaag ttattttaac attatttgtt ttattatcta ttggaatatt tgcaaatgat      60
gagattattt cagagttaaa aggacttaat gctgagtatg aaaatttagt aaaagaagaa     120
gaagctagat tcaaaaaga aaaagaactt tctgaaagag cagcagctca aaatgttaaa     180
ttggctgaat taaaagcaag cattgaagaa aaattgttag cagctccaga gaaagaaaa     240 acaaaatttt taaagatac ttttgatggt ttagtgaaag attattcaaa atatttaagt     300
caaataaatg aaaaaatagc tgaaaatact gaaatagtaa gtaattttga aaaaattcaa     360
aaaataagat ag                                                         372

<210> SEQ ID NO 13
<211> LENGTH: 129
<212> TYPE: PRT
<213> ORGANISM: Fusobacterium nucleatum

<400> SEQUENCE: 13

Met Lys Lys Phe Leu Leu Leu Ala Val Leu Ala Val Ser Ala Ser Ala
1               5                   10                  15

Phe Ala Ala Asn Asp Ala Ala Ser Leu Val Gly Glu Leu Gln Ala Leu
            20                  25                  30

Asp Ala Glu Tyr Gln Asn Leu Ala Asn Gln Glu Glu Ala Arg Phe Asn
        35                  40                  45

Glu Glu Arg Ala Gln Ala Asp Ala Ala Arg Gln Ala Leu Ala Gln Asn
    50                  55                  60

Glu Gln Val Tyr Asn Glu Leu Ser Gln Arg Gln Arg Leu Gln Ala
65                  70                  75                  80

Glu Ala Asn Thr Arg Phe Tyr Lys Ser Gln Tyr Gln Asp Leu Ala Ser
                85                  90                  95

Lys Tyr Glu Asp Ala Leu Lys Lys Leu Glu Ser Glu Met Glu Gln Gln
            100                 105                 110

Lys Ala Ile Ile Ser Asp Phe Glu Lys Ile Gln Ala Leu Arg Ala Gly
        115                 120                 125

Asn

<210> SEQ ID NO 14
<211> LENGTH: 390
<212> TYPE: DNA
<213> ORGANISM: Fusobacterium nucleatum

<400> SEQUENCE: 14

```
atgaaaaaat ttttattatt agcagtatta gctgtttctg cttcagcatt cgcagcaaat      60
gatgcagcaa gttagtagg tgaattacaa gcattagatg ctgaatacca aaacttagca     120
aatcaagaag aagcaagatt caatgaagaa agagcacaag ctgacgctgc tagacaagca     180
ctagcacaaa tgaacaagt ttacaatgaa ttatctcaaa gagctcaaag acttcaagct     240
gaagctaaca caagatttta taaatctcaa taccaagatc tagcttctaa atatgaagac     300
gctttaaaga aattagaatc tgaaatggaa caacaaaaag ctattatttc tgattttgaa     360
aaaattcaag ctttaagagc tggtaactaa                                      390
```

<210> SEQ ID NO 15
<211> LENGTH: 67
<212> TYPE: PRT
<213> ORGANISM: Homo sapiens

<400> SEQUENCE: 15

Met Arg Ile His Tyr Leu Leu Phe Ala Leu Leu Phe Leu Phe Leu Val
 1               5                  10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 16
<211> LENGTH: 204
<212> TYPE: DNA
<213> ORGANISM: Homo sapiens

<400> SEQUENCE: 16

```
atgaggatcc attatcttct gtttgctttg ctcttcctgt ttttggtgcc tgttccaggt      60
catggaggaa tcataaacac attacagaaa tattattgca gagtcagagg cggccggtgt     120
gctgtgctca gctgccttcc aaaggaggaa cagatcggca agtgctcgac gcgtggccga     180
aaatgctgcc gaagaaagaa ataa                                             204
```

<210> SEQ ID NO 17
<211> LENGTH: 337
<212> TYPE: DNA
<213> ORGANISM: Homo sapiens

<400> SEQUENCE: 17

```
tgagtctcag cgtggggtga agcctagcag ctatgaggat ccattatctt ctgtttgctt      60
```

-continued

```
tgctcttcct gtttttggtg cctgtcccag gtcatggagg aatcataaac acattacaga      120
aatattattg cagagtcaga ggcggccggt gtgctgtgct cagctgcctt ccaaaggagg      180
aacagatcgg caagtgctcg acgcgtggcc gaaaatgctg ccgaagaaag aaataaaaac      240
cctgaaacat gacgagagtg ttgtaaagtg tggaaatgcc ttcttaaagt ttataaaagt      300
aaaatcaaat tacattttttt tttcaaaaaa aaaaaa                               337
```

<210> SEQ ID NO 18
<211> LENGTH: 266
<212> TYPE: DNA
<213> ORGANISM: Homo sapiens

<400> SEQUENCE: 18

```
catccagtct cagcgtgggg tgaagcctag cagctatgag gatccattat cttctgtttg       60
ctttgctctt cctgtttttg gtgcctgttc caggtcatgg aggaatcata aacacattac      120
agaaatatta ttgcagagtc agaggcggcc ggtgtgctgt gctcagctgc cttccaaagg      180
aggaacagat cggcaagtgc tcgacgcgtg gccgaaaatg ctgccgaaga agaaataaa       240 aaccctgaaa catgacgaga gtgttg                                          266
```

<210> SEQ ID NO 19
<211> LENGTH: 856
<212> TYPE: PRT
<213> ORGANISM: HIV

<400> SEQUENCE: 19

```
Met Arg Val Lys Glu Lys Tyr Gln His Leu Trp Arg Trp Gly Trp Arg
  1               5                  10                  15

Trp Gly Thr Met Leu Leu Gly Met Leu Met Ile Cys Ser Ala Thr Glu
             20                  25                  30

Lys Leu Trp Val Thr Val Tyr Tyr Gly Val Pro Val Trp Lys Glu Ala
         35                  40                  45

Thr Thr Thr Leu Phe Cys Ala Ser Asp Ala Lys Ala Tyr Asp Thr Glu
     50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
```

-continued

```
            225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
            370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
        530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
        610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655
```

-continued

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 20
<211> LENGTH: 483
<212> TYPE: PRT
<213> ORGANISM: HIV

<400> SEQUENCE: 20

Ser Ala Thr Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
                20                  25                  30

Tyr Asp Thr Glu Val His Asn Val Trp Ala Thr His Ala Cys Val Pro
            35                  40                  45

Thr Asp Pro Asn Pro Gln Glu Val Val Leu Val Asn Val Thr Glu Asn
        50                  55                  60

Phe Asn Met Trp Lys Asn Asp Met Val Glu Gln Met His Glu Asp Ile
65                  70                  75                  80

Ile Ser Leu Trp Asp Gln Ser Leu Lys Pro Cys Val Lys Leu Thr Pro
                85                  90                  95

Leu Cys Val Ser Leu Lys Cys Thr Asp Leu Lys Asn Asp Thr Asn Thr
            100                 105                 110

Asn Ser Ser Ser Gly Arg Met Ile Met Glu Lys Gly Glu Ile Lys Asn
        115                 120                 125

Cys Ser Phe Asn Ile Ser Thr Ser Ile Arg Gly Lys Val Gln Lys Glu
    130                 135                 140

Tyr Ala Phe Phe Tyr Lys Leu Asp Ile Ile Pro Ile Asp Asn Asp Thr
145                 150                 155                 160

Thr Ser Tyr Lys Leu Thr Ser Cys Asn Thr Ser Val Ile Thr Gln Ala

```
            165                 170                 175
Cys Pro Lys Val Ser Phe Glu Pro Ile Pro Ile His Tyr Cys Ala Pro
            180                 185                 190

Ala Gly Phe Ala Ile Leu Lys Cys Asn Asn Lys Thr Phe Asn Gly Thr
        195                 200                 205

Gly Pro Cys Thr Asn Val Ser Thr Val Gln Cys Thr His Gly Ile Arg
    210                 215                 220

Pro Val Val Ser Thr Gln Leu Leu Leu Asn Gly Ser Leu Ala Glu Glu
225                 230                 235                 240

Glu Val Val Ile Arg Ser Val Asn Phe Thr Asp Asn Ala Lys Thr Ile
                245                 250                 255

Ile Val Gln Leu Asn Thr Ser Val Glu Ile Asn Cys Thr Arg Pro Asn
            260                 265                 270

Asn Asn Thr Arg Lys Arg Ile Arg Ile Gln Arg Gly Pro Gly Arg Ala
        275                 280                 285

Phe Val Thr Ile Gly Lys Ile Gly Asn Met Arg Gln Ala His Cys Asn
    290                 295                 300

Ile Ser Arg Ala Lys Trp Asn Asn Thr Leu Lys Gln Ile Ala Ser Lys
305                 310                 315                 320

Leu Arg Glu Gln Phe Gly Asn Asn Lys Thr Ile Ile Phe Lys Gln Ser
                325                 330                 335

Ser Gly Gly Asp Pro Glu Ile Val Thr His Ser Phe Asn Cys Gly Gly
            340                 345                 350

Glu Phe Phe Tyr Cys Asn Ser Thr Gln Leu Phe Asn Ser Thr Trp Phe
        355                 360                 365

Asn Ser Thr Trp Ser Thr Glu Gly Ser Asn Asn Thr Glu Gly Ser Asp
    370                 375                 380

Thr Ile Thr Leu Pro Cys Arg Ile Lys Gln Ile Ile Asn Met Trp Gln
385                 390                 395                 400

Lys Val Gly Lys Ala Met Tyr Ala Pro Pro Ile Ser Gly Gln Ile Arg
                405                 410                 415

Cys Ser Ser Asn Ile Thr Gly Leu Leu Leu Thr Arg Asp Gly Gly Asn
            420                 425                 430

Ser Asn Asn Glu Ser Glu Ile Phe Arg Pro Gly Gly Gly Asp Met Arg
        435                 440                 445

Asp Asn Trp Arg Ser Glu Leu Tyr Lys Tyr Lys Val Val Lys Ile Glu
    450                 455                 460

Pro Leu Gly Val Ala Pro Thr Lys Ala Lys Arg Arg Val Val Gln Arg
465                 470                 475                 480

Glu Lys Arg

<210> SEQ ID NO 21
<211> LENGTH: 345
<212> TYPE: PRT
<213> ORGANISM: HIV

<400> SEQUENCE: 21

Ala Val Gly Ile Gly Ala Leu Phe Leu Gly Phe Leu Gly Ala Ala Gly
 1               5                  10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
```

-continued

```
                50                    55                    60
Leu Gln Ala Arg Ile Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Glu Gln Ile Trp
                100                 105                 110

Asn His Thr Thr Trp Met Glu Trp Asp Arg Glu Ile Asn Asn Tyr Thr
                115                 120                 125

Ser Leu Ile His Ser Leu Ile Glu Glu Ser Gln Asn Gln Gln Glu Lys
                130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
                180                 185                 190

Ile Val Asn Arg Val Arg Gln Gly Tyr Ser Pro Leu Ser Phe Gln Thr
                195                 200                 205

His Leu Pro Thr Pro Arg Gly Pro Asp Arg Pro Glu Gly Ile Glu Glu
                210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
                260                 265                 270

Leu Leu Gly Arg Arg Gly Trp Glu Ala Leu Lys Tyr Trp Trp Asn Leu
                275                 280                 285

Leu Gln Tyr Trp Ser Gln Glu Leu Lys Asn Ser Ala Val Ser Leu Leu
                290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
                340                 345
```

US 7,442,375 B2

COMPOSITIONS OF BETA-DEFENSIN INDUCING AGENTS

RELATED APPLICATIONS

This application is a continuation-in-part of U.S. patent application Ser. No. 10/737,288, filed Dec. 15, 2003, which claims the benefit of the filing date of U.S. Provisional Application No. 60/433,099, filed Dec. 13, 2002, the specifications of which are hereby incorporated by reference in their entirety.

FUNDING

Work described herein was funded, in part, by NIH grants RO-1 DE12589, RO-1 DE13992, and RO-1 DE015510. The United States government has certain rights in the invention.

BACKGROUND

Fully satisfactory treatments for Human Immunodeficiency Virus (HIV) have not yet been discovered. Mixtures of agents that target the reverse transcriptase and the protease have proven to be highly effective. However, patients are forced to self-administer a large number of medications on a tightly regulated schedule. Failure to follow the prescribed regimen results in rapid generation of drug-resistant HIV mutants. Antiviral agents taken individually are ineffective, largely because of the rapid rate at which the infecting virus population becomes resistant. For this reason, single and multiple drug therapies are often denied to patients that seem unlikely to be able to follow the required dosing schedule. In addition, many protease inhibitors are expensive to manufacture and are not widely available in regions where HIV is rampant, including sub-Saharan Africa and South-East Asia.

The present application provides novel agents for the treatment of HIV and other viral infections associated with certain chemokine receptors, e.g., CXCR4.

SUMMARY OF THE INVENTION

In certain aspects, the invention relates to methods and compositions for preventing, treating or otherwise diminishing an HIV infection or decreasing the likelihood of contracting an HIV infection.

An aspect of the invention provides a method for treating or inhibiting an HIV infection in a subject, comprising administering to the subject an effective amount of a beta defensin (BD) agent, a BD-inducing agent, an agent that potentiates the interaction between a BD-polypeptide and a chemokine receptor (e.g., CXCR4), or an agent that potentiates the interaction between a BD-polypeptide and a virion (e.g., an HIV virion).

Another aspect of the invention provides a method for inhibiting or preventing the contraction of an HIV infection in a subject, particularly an at-risk subject, comprising administering to the subject an effective amount of a BD agent, a BD-inducing agent, an agent that potentiates the interaction between a BD-polypeptide and a chemokine receptor (e.g., CXCR4), or an agent that potentiates the interaction between a BD-polypeptide and a virion (e.g., an HIV virion).

In certain aspects, the invention also provides a method for inhibiting HIV entry into a cell, the method comprising contacting the cell with an effective amount of a BD agent, a BD-inducing agent, an agent that potentiates the interaction between a BD-polypeptide and a chemokine receptor or fragments thereof (e.g., CXCR4), or an agent that potentiates the interaction between a BD-polypeptide or its fragments and a virion (e.g., an HIV virion).

In certain aspects, the invention also provides a method for inhibiting HIV entry into a cell, the method comprising contacting the HIV with an effective amount of a BD agent. The method may further include contacting the cell an agent that potentiates the interaction between a BD-polypeptide or its fragment and a chemokine receptor or its fragment or an HIV virion.

A BD agent of the invention may be a naturally occurring BD polypeptide, a peptidomimetic, or variant thereof, or a nucleic acid encoding same. In preferred embodiments, a BD agent of the invention is preferably a human BD (HBD) agent. In certain embodiments, an HBD agent of the invention comprises a human beta defensin-2 (HBD-2) agent. In certain embodiments, an HBD-2 agent is a polypeptide comprising an amino acid sequence at least 80%, 85%, 90%, 95%, 97%, or 99% identical to an amino acid sequence selected from the group consisting of: SEQ ID NO:1 and SEQ ID NO:2. In certain embodiments, an HBD-2 agent is a polypeptide encoded by a nucleic acid that is at least 80%, 85%, 90% 95%, 97%, or 99% identical to a nucleic acid selected from the group consisting of: SEQ ID NOs:4-7. In certain embodiments, an HBD agent of the invention comprises a human beta defensin-3 (HBD-3) agent. In certain embodiments, an HBD-3 agent is a polypeptide comprising an amino acid sequence at least 80%, 85%, 90%, 95%, 97%, or 99% identical to an amino acid sequence as set forth in SEQ ID NO:15. In certain embodiments, an HBD-3 agent is a polypeptide encoded by a nucleic acid that is at least 80%, 85%, 90%, 95%, 97%, or 99% identical to a nucleic acid selected from the group consisting of: SEQ ID NOs:16-18.

In certain embodiments, the invention provides a BD-inducing agent that induces or increases the expression of a BD-polypeptide. In certain embodiments, a BD-inducing agent of the invention induces or increases expression in a cell of a BD-2 polypeptide, a BD-3 polypeptide, or both. Preferably, a BD-inducing agent induces or increases expression in a cell of an HBD-2 polypeptide, an HBD-3 polypeptide, or both. In certain embodiments, a BD-inducing agent of the invention is a polypeptide comprising an amino acid sequence at least 80%, 85%, 90%, 95%, 97%, or 99% identical to an amino acid sequence selected from the group consisting of SEQ ID NOs:3, 9, 11, and 13. In certain embodiments, a BD-inducing agent is a polypeptide encoded by a nucleic acid that is at least 80%, 85%, 90%, 95%, 97%, or 99% identical to a nucleic acid having a nucleotide sequence selected from the group consisting of SEQ ID NOs:8, 10, 12, and 14. In certain embodiments, the methods and compositions disclosed herein may employ, as a BD-inducing agent, a FAD-I polypeptide.

In certain embodiments, the methods and compositions disclosed herein may employ a BD-inducing agent, such as a viral protein. In certain embodiments, the viral protein is an HIV protein such as for example gp120 or gp41. In certain embodiments, an HIV protein is a polypeptide comprising an amino acid sequence at least 80%, 85%, 90%, 95%, 97%, or 99% identical to an amino acid sequence of SEQ ID NO:19, 20, or 21. In certain embodiments, an HIV protein is a polypeptide obtained by expressing a nucleic acid that is at least 80%, 85%, 90%, 95%, 97%, or 99% identical to a nucleic acid of SEQ ID NO:19, 20, or 21 in a cell. In certain embodiments, an HIV protein is a polypeptide encoded by a nucleic acid that is at least 80%, 85%, 90%, 95%, 97%, or 99% identical to a nucleic acid of SEQ ID NO: 19, 20, or 21.

In certain embodiments, the invention also provides an agent and methods of using same that can potentiate the interaction between a BD-polypeptide and a chemokine receptor. Such an agent may be a polypeptide, a nucleic acid, a peptidomimetic, or a small molecule. In preferred embodiments, an agent of the invention potentiates the interaction between a BD-polypeptide and CXCR4. The BD-polypeptide is preferably a HBD-polypeptide. In certain embodiments, an agent of the invention potentiates the interaction between a HBD-2 polypeptide and CXCR4 or fragments thereof. In certain embodiments, an agent of the invention potentiates the interaction between a HBD-3 polypeptide and CXCR4. The same agent may potentiate the interactions between CXCR4 and HBD-2 polypeptide (or fragments thereof) and between CXCR4 and HBD-3 polypeptide (or fragments thereof).

In certain embodiments, the invention also provides an agent and methods thereof that can potentiate the interaction between a BD-polypeptide and a virion. In preferred embodiments, an agent of the invention potentiates the interaction between a BD-polypeptide and an HIV virion.

In certain embodiments, the invention provides methods and compositions for treating a subject susceptible to or having an HIV infection, where the HIV is a strain that associates with CXCR or is an X4-tropic HIV.

In preferred embodiments, an agent of the invention has a 50% effectiveness at a concentration of about 10 µM or less.

In certain embodiments, the invention provides systemic administration to a subject of an agent of the invention. Systemic administration may include direct administration to the bloodstream. The invention also provides methods and compositions suitable for such systemic administration.

In certain embodiments, the invention also provides local administration to a subject of an agent of the invention. Local administration may include administration to a portion of the body, for example the mouth, the nasopharyngeal tract, the anus, the vagina, the penis, the skin, or the eye. Local administration may include administration to a mucous membrane. An agent of the invention may be formulated as a mouthwash, a toothpaste, an aerosol, a rectal or vaginal suppository, a rectal or vaginal cream, a rectal or vaginal film, a skin lotion, a condom, an eye drop, or an eye ointment.

In certain embodiments, the invention further provides administering an agent of the invention in combination with an additional antiviral agent. In certain embodiments, the antiviral agent targets a portion of the HIV virus, for example, an HIV protease or an HIV reverse transcriptase.

In certain aspects, the invention also provides pharmaceutical compositions having antiviral activity. A pharmaceutical composition of the invention may comprise a BD-inducing agent and a pharmaceutically acceptable carrier. Alternatively, a pharmaceutical composition of the invention comprises a pharmaceutically acceptable carrier and an agent that can potentiate the interaction between a BD-polypeptide and a chemokine receptor. Yet another pharmaceutical composition of the invention comprises a BD agent and a pharmaceutically acceptable carrier.

In certain embodiments, a pharmaceutical composition of the invention comprises a BD-inducing agent, an agent that potentiates the interaction between a BD-polypeptide, and a chemokine receptor, preferably CXCR4, and a pharmaceutically acceptable carrier.

In certain embodiments, a pharmaceutical composition of the invention comprises a BD agent, an agent that potentiates the interaction between a BD-polypeptide and a chemokine receptor, preferably CXCR4, and a pharmaceutically acceptable carrier.

A pharmaceutically acceptable carrier to formulate a pharmaceutical composition of the invention may be, for example, suitable for systemic administration or for local administration.

In a further embodiment, the invention provides a kit comprising a pharmaceutical composition of the invention and further comprising an antiviral agent. The antiviral agent preferably targets a portion of the HIV virus, for example, an HIV protease or an HIV reverse transcriptase.

Another aspect of the invention provides methods of optimizing an agent of the invention. For optimization, an agent may be known or identified by a method of the invention. A method of optimizing includes a step of evaluating an agent of the invention for the agent's efficacy in preventing HIV infection or contraction in a subject, treating a subject susceptible to or having an HIV infection, or inhibiting HIV entry into a cell.

In certain embodiments, the invention provides a method of optimizing a BD-inducing agent having antiviral activity comprising identifying an agent that can induce or increase expression of a BD-polypeptide in a cell and further evaluating the antiviral efficacy of the agent. The level of expression of a BD-polypeptide may vary due to changes at different stages, for example, transcription, translation, or posttranslational processing. A cell utilized in a method of the invention can express an endogenous BD polypeptide, preferably, an endogenous BD-2 or BD-3 polypeptide. Alternatively, a cell utilized in a method of the invention expresses a reporter gene operably linked to a BD promoter nucleic acid, preferably, a BD-2 or BD-3 promoter, and more preferably, an HBD-2 or HBD-3 promoter. A BD-inducing agent of the invention may be, for example, a polypeptide, a peptidomimetic, a nucleic acid, or a small molecule.

The invention further provides a method of identifying a BD-inducing agent comprising providing cells capable of expressing a BD-polypeptide, contacting said cells with a candidate agent and determining the level of expression of said BD-polypeptide in the presence of said candidate agent; an increase in the expression level of said BD-polypeptide in comparison to appropriate control level is indicative of a BD-inducing agent. Alternatively, the invention provides a method of identifying a BD-inducing agent comprising providing cells capable of expressing a reporter gene operably linked to a BD promoter nucleic acid, contacting said cells with a candidate agent, and determining the level of expression of said reporter gene in the presence of said candidate agent; an increase in the expression of said reporter gene in comparison to appropriate control level expression of said reporter gene is indicative of a BD-inducing agent.

In a preferred embodiment, the invention provides a method of identifying a BD-inducing agent that induces or increases expression of a human BD (HBD)-polypeptide. Preferably, a BD-inducing agent of the invention induces or increases expression of a HBD-2 polypeptide or a HBD-3 polypeptide. Preferably, a BD-inducing agent of the invention induces or increases expression of at least two different BD-polypeptides, for example, both HBD-2 and HBD-3 polypeptides. A method of optimizing a BD-inducing agent may further comprise the step of preparing a pharmaceutical composition comprising said BD-inducing agent.

Some embodiments of the invention provide a method of optimizing an agent that potentiates the interaction between a BD-polypeptide and a chemokine receptor. In certain embodiments, a method of the invention comprises identifying an agent that can potentiate the interaction between a BD-polypeptide and a chemokine receptor and further evaluating the identified agent for its efficacy in preventing HIV contraction by a subject, inhibiting HIV entry into a cell, or treating an HIV infection in a subject. An agent of the invention that potentiates the interaction between a BD-polypeptide and a chemokine receptor may be, for example, a polypeptide, a peptidomimetic, a nucleic acid, or a small molecule. A method of optimizing an agent that potentiates the interaction between a BD-polypeptide and a chemokine receptor may further include preparing a pharmaceutical composition comprising said agent and a pharmaceutically suitable carrier.

In further embodiments, the invention provides a method of identifying an agent that can potentiate the interaction between a BD-polypeptide and a chemokine receptor, said method comprising determining the interaction of said chemokine receptor and said BD-polypeptide in the presence and absence of a candidate agent; an increase in the interaction of said BD-polypeptide with said chemokine receptor in the presence of said candidate agent is indicative of an agent that potentiates the interaction between said BD-polypeptide and said chemokine receptor. In a preferred embodiment, a chemokine receptor of the invention is CXCR4. Certain embodiments of the invention utilize a portion of a wild-type CXCR4, said portion is sufficient for the interaction with a BD-polypeptide. Certain embodiments of the invention utilizes a chemokine receptor, preferably CXCR4, that is expressed on the surface of a cell.

In certain embodiments, the invention provides a method of identifying an agent that potentiates the interaction between a BD-polypeptide and a virion, comprising determining the interaction of said virion and said BD-polypeptide in the presence and absence of a candidate agent; an increase in the interaction of said BD-polypeptide with said virion in the presence of said candidate agent is indicative of an agent that potentiates the interaction between said BD-polypeptide and said virion. Preferred embodiments employ an agent that potentiates the interaction between an HIV virion and a BD-polypeptide.

A preferred embodiment of the invention utilizes a BD-polypeptide that is a human BD-polypeptide (HBD). More preferably, an HBD-polypeptide of the invention is an HBD-2 polypeptide or an HBD-3 polypeptide.

In certain embodiments, an HBD-2 polypeptide of the invention comprises an amino acid sequence at least 80%, 85%, 90%, 95%, 97%, or 99% identical to an amino acid sequence selected from the group consisting of: SEQ ID NO:1 and SEQ ID NO:2. In certain embodiments, an HBD-2 polypeptide is encoded by a nucleic acid that is at least 80%, 85%, 90%, 95%, 97%, or 99% identical to a nucleic acid selected from the group consisting of: SEQ ID NOs:4-7.

In certain embodiments, an HBD-3 polypeptide is a polypeptide comprising an amino acid sequence at least 80%, 85%, 90%, 95%, 97%, or 99% identical to an amino acid sequence as set forth in SEQ ID NO:15. In certain embodiments, an HBD-3 polypeptide is a polypeptide encoded by a nucleic acid that is at least 80%, 85%, 90%, 95%, 97%, or 99% identical to a nucleic acid selected from the group consisting of: SEQ ID NOs:16-18.

Some embodiments of the invention also contemplate methods of optimizing a BD agent. A BD agent of the invention may be known or identified and has antimicrobial and antiviral activities similar to those of a BD-polypeptide of the invention, preferably, a BD-2 or BD-3 polypeptide, and more preferably, an HBD-2 or HBD-3 polypeptide. A method of optimizing a BD agent may comprise evaluating said BD agent for its antiviral activity, preferably anti-HIV activities.

In certain embodiments, the invention provides a method of identifying a BD agent comprising selecting a candidate agent that can interact with a chemokine receptor, preferably a CXCR4, and determining whether the selected candidate agent binds HIV virion. Alternatively, a method of identifying a BD agent comprises determining whether the selected candidate agent inhibits HIV entry into a cell. A method of identifying a BD agent may further comprise determining whether the selected candidate agent has antimicrobial activity. A method of optimizing a BD agent may further include preparing a pharmaceutical composition comprising said BD agent and a pharmaceutically suitable carrier.

A BD agent of the invention may be, for example, a polypeptide, a peptidomimetic, a nucleic acid, or a small molecule. Preferably, a BD agent comprises a BD-polypeptide. Preferred embodiments of the invention employ a human BD (HBD)-polypeptide as a BD agent. Certain embodiments may employ peptidomimetics based on a BD-polypeptide, preferably an HBD-polypeptide, as BD agents.

Preferably, a BD agent comprises an HBD-2 polypeptide, its fragment or variant, or a peptidomimetic based on an HBD-2 polypeptide. Preferred embodiments utilize an HBD-2 polypeptide comprising an amino acid sequence at least 80%, 85%, 90%, 95%, 97%, or 99% identical to an amino acid sequence selected from the group consisting of: SEQ ID NO:1 and SEQ ID NO:2. Alternatively, an HBD-2 polypeptide is encoded by a nucleic acid that is at least 80%, 85%, 90%, 95%, 97%, or 99% identical to a nucleic acid selected from the group consisting of: SEQ ID NOs:4-7.

Preferably, a BD agent comprises an HBD-3 polypeptide, its fragment or variant, or a peptidomimetic based on an HBD-3 polypeptide. Preferred embodiments utilize an HBD-3 polypeptide comprising an amino acid sequence at least 80%, 85%, 90%, 95%, 97%, or 99% identical to an amino acid sequence as set forth in SEQ ID NO:15. Alternatively, an HBD-3 polypeptide is encoded by a nucleic acid that is at least 80%, 85%, 90%, 95%, 97%, or 99% identical to a nucleic acid selected from the group consisting of: SEQ ID NOs:16-18.

Anti-HIV-1 activity of hBD in GHOST X4/R5 cells using fluorescence microscopy. (c) Anti-HIV-1 activity of hBD measured by RT activity in cell-free culture supernatant, relative to the positive control (i.e., HIV-1 infection in the absence of hBD). (d) Antiretroviral activity of hBD against CXCR4- and CCR5-tropic HIV-1 strains in three different environments: DMEM+10% FBS (complete medium); DMEM alone (Medium no FBS); 10 mM PB. Viruses were incubated with 20 μg/ml of each hBD for 1 h in each condition and used to infect CEM X4/R5 cells as described. Results are representative of three independent experiments.

Figure 5:
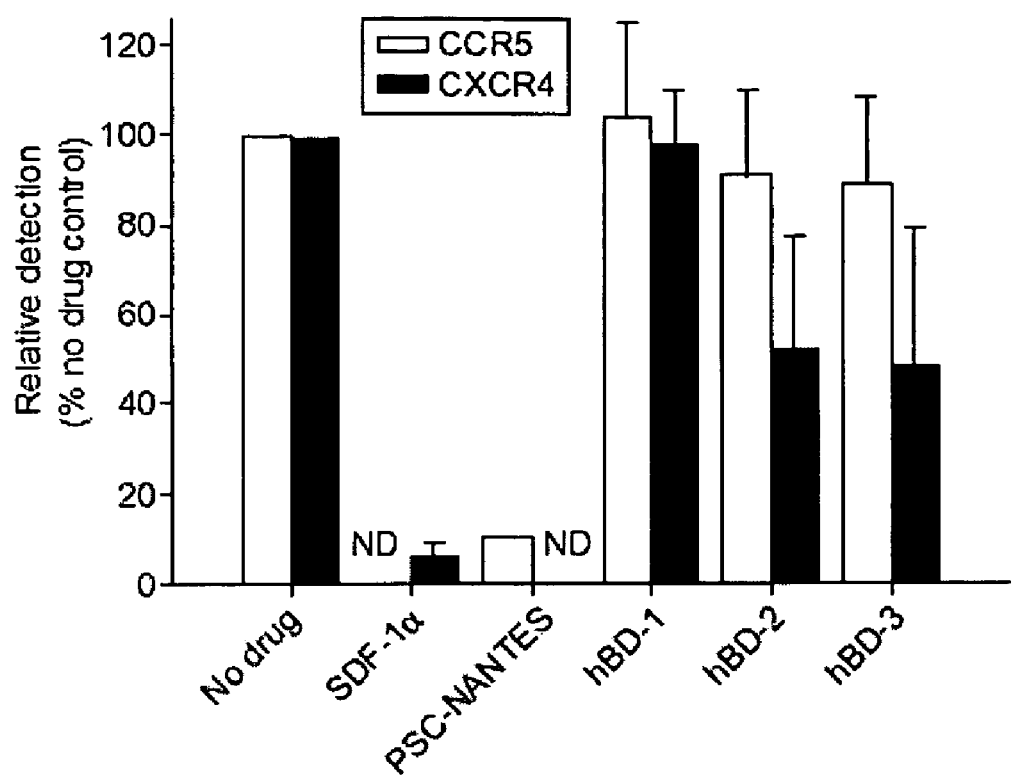

FIG. 5 shows that hBD-2 and -3 downmodulate CXCR4. Unstimulated PBMC were treated for 3 hrs with hBD-1, -2, or -3 (30 μg/ml) in DMEM (high salt) in the absence of FBS. The CXCR4 natural ligand SDF-1AE (2 μg/ml) and the CCR5 antagonist PSC-RANTES (100 nM) were used as positive controls. CXCR4 and CCR5 surface expression was calculated using known ratios of QuantiBRITE-PE beads (Becton Dickenson) by flow cytometry. Results are the means of seven experiments±SD.

Figure 6:
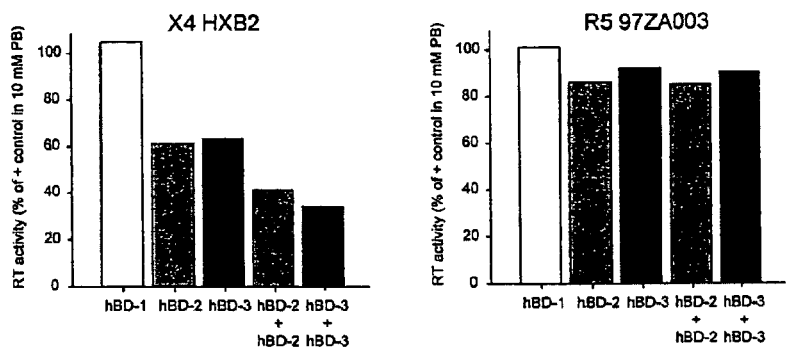
Figure 6:
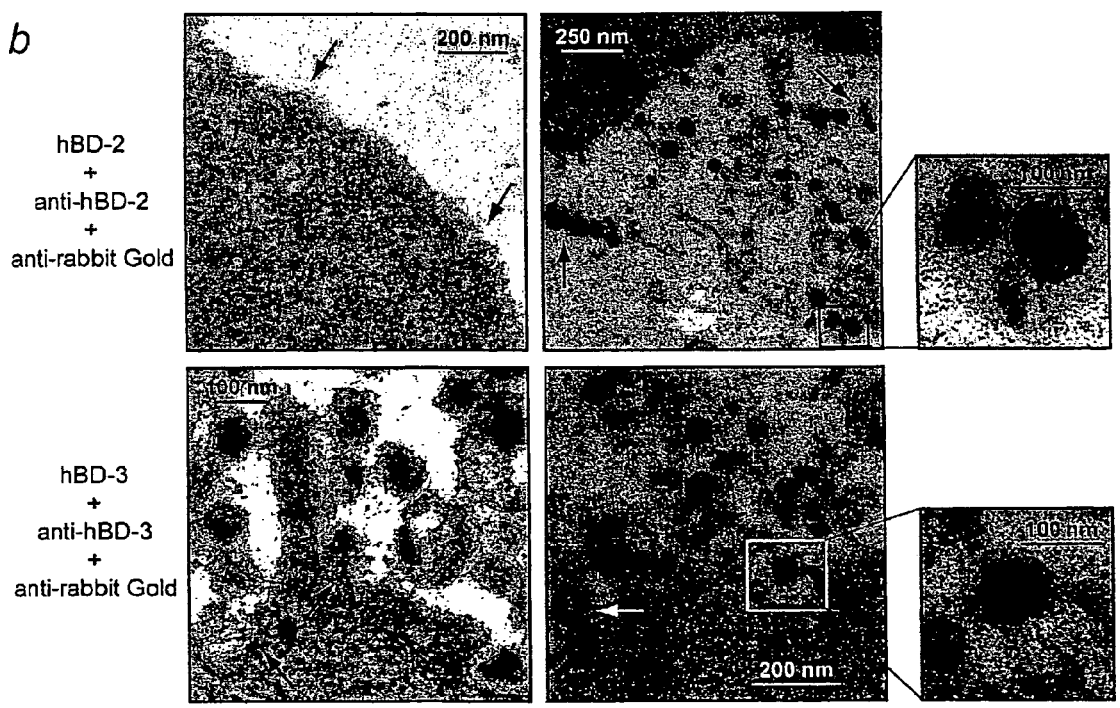

FIG. 6 shows that hBD-2 and -3 interact directly with HIV-1 and inhibit HIV-1 infectivity irreversibly. (a) CXCR4 tropic HXB2 and CCR5 tropic 97ZA003 HIV-1 strains were incubated with 20 μg/ml hBD-1, -2, or -3 in 10 mM PB for 1 h. Virions were pelleted, washed extensively with PBS and used to infect GHOST X4/R5 cells. RT activity was measured 48 h post-infection. The final two columns represent an additional 20 μg/ml of hBD-2 or -3 during infection. (b) Immunoelectron microscopy analysis showing the interaction of hBD-2 and -3 with HIV-1 and with MT4 cell membrane. X4 HIV-1 HXB2 strain and MT4 cells were incubated with hBD-2 or -3 (20 μg/ml), 37° C., 1 h. Polyclonal anti-hBD-2 or -3 antibodies were added, followed by addition of secondary IgG conjugated with 10-nm gold particles. Arrows indicate hBD-2 and -3 localization to virions and cell membrane.

DETAILED DESCRIPTION OF THE INVENTION

1. Overview

In certain aspects, the present invention relates to the discovery that beta-defensin-2 ("BD-2"), beta-defensin-3 ("BD-3"), and related polypeptides, referred to herein as BD-polypeptides, inhibit the infection of cells by HIV. The disclosure also provides methods and compositions for treating and preventing HIV infections. While it is expected that a BD-polypeptide will achieve antiviral effects primarily by preventing virion entry into a target cell, such a polypeptide may act in other ways and the invention should not be limited to any particular mechanism of action. In addition to providing for the use of BD-polypeptides as direct antiviral agents, the invention provides for the use of various BD-related agents, such as agents that induce or increase beta-defensin production, potentiate the interaction between a BD-polypeptide and a chemokine receptor, and potentiate the interaction between a BD-polypeptide and an HIV virion.

Defensins represent a family of small (3-5 kDa) cationic peptides having antimicrobial activities. To date, at least three subfamilies of defensins have been identified: alpha defensins, beta defensins, and the cyclic theta defensins (for review, see, e.g., Cole, A. M., Minidefensins and Other Antimicrobial Peptides: Candidates Anti-HIV Microbicides, Expert Opin. Ther. Targets (2003) 7:32941). Alpha and beta defensins have a characteristic beta-sheet structure stabilized by two to three intramolecular disulfide bonds, but they differ in size and in the connectivity of their six cysteine residues. Alpha-defensins are 29 to 35-amino acid peptides having three intramolecular disulfide bonds through Cys1-Cys6, Cys2-Cys4, and Cys3-Cys5, whereas mature beta defensins are up to 45-residue peptides having disulfide connectivity with Cys1-Cys5, Cys2-Cys4, and Cys3-Cys6. Defensins are microbistatic or microbicidal against a wide spectrum of Gram-positive and Gram-negative bacteria, fungi, yeast, and some enveloped viruses. More specifically, human beta defensins-1 and -2 are predominantly active against Gram-negative bacteria, human beta-defensin-3 demonstrates a salt-insensitive broad spectrum of potent antimicrobial activity against pathogenic microbes including Gram-positive bacteria, and human beta defensin-4 has a specific salt-sensitive spectrum of antimicrobial activity. Alpha defensins also exhibit a tissue-specific expression pattern different from beta defensins, which are expressed predominantly in epithelia. Another important differentiating feature between alpha- and beta-defensins is that while the former are cytotoxic to mammalian cells when released from protective granules, the latter are not.

To date, more than 30 human beta-defensins have been discovered based on human genome mining. Human beta defensin (HBD)-1 is constitutively expressed by epithelia, while the expression of HBD-2, -3, and -4 is induced upon stimulation by inflammatory mediators, such as TNF-α and IL-1β, and contact with bacteria including mucoid forms of *Psudomonas aeruginosa* bacteria.

Accordingly, agents that induce or increase beta-defensin production and agents that modulate activities of a beta-defensin can be used as preventative or therapeutic agents for a wide range of disorders.

2. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

A "chimeric polypeptide" or "fusion polypeptide" is a fusion of a first amino acid sequence with a second amino acid sequence where the first and second amino acid sequences are not naturally present in a single polypeptide chain.

The term "compound" used herein is meant to include, but not limited to, peptides, nucleic acids, carbohydrates, small organic molecules, natural product extract libraries, and any other molecules (including, but not limited to, chemicals, metals and organometallic compounds).

The term "ED50" means the dose of a drug which produces 50% of its maximum response or effect.

An "effective amount" of, e.g., an agent of the invention, with respect to the subject method of treatment, refers to an amount of the activator in a pharmaceutical preparation which, when applied as part of a desired dosage regimen brings about inhibition of viral (e.g., HIV) infection, viral (e.g., HIV) entry into a cell, or other viral (e.g., HIV) activities, according to clinically acceptable standards.

"Expression" of a BD-polypeptide refers to the amount of mature BD-polypeptide produced by a cell. Accordingly, the level of expression can be modulated at different stages such as transcription, translation, and posttranslational processing.

An "expression construct" is any recombinant nucleic acid that includes an expressible nucleic acid and regulatory elements sufficient to mediate expression in a suitable host cell.

For example, an expression construct may contain a promoter or other RNA polymerase contact site, a transcription start site or a transcription termination sequence. An expression construct for production of a protein may contain a translation start site, such as an ATG codon, a ribosome binding site, such as a Shine-Dalgarno sequence, or a translation stop codon.

The term "heterologous" as used in describing a nucleic acid with respect to another nucleic acid means that the two nucleic acids are not normally operably linked to each other or do not naturally occur in adjacent positions.

The term "LD50" means the dose of a drug which is lethal in 50% of test subjects.

The term "nucleic acid" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single (sense or antisense) and double-stranded polynucleotides. Nucleic acids may include unconventional modifications to any portion, including, for example, the sugar phosphate backbone or the base portion.

The term "or" is used herein to mean, and is used interchangeably with, the term "and/or", unless context clearly indicates otherwise.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric or electronic nature), then the molecules can be referred to as homologous (similar) at that position. Expression as a percentage of homology/similarity or identity refers to a function of the number of identical or similar amino acids at positions shared by the compared sequences. Various alignment algorithms or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified," it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "recombinant nucleic acid construct" includes any nucleic acid comprising at least two sequences which are not adjacent on a nucleic acid strand in nature. A recombinant nucleic acid may be generated in vitro, for example by using the methods of molecular biology, or in vivo, for example by insertion of a nucleic acid at a novel chromosomal location by homologous or non-homologous recombination.

A "patient" or "subject" to be treated by the subject method can mean either a human or non-human animal.

The term "prevent," "preventing," or "prevention" as used herein means reducing the probability or risk of viral (e.g., HIV) contraction by a subject or viral (e.g., HIV) infection in a subject, or delaying the onset of a condition relating to a viral (e.g., HIV) infection in the subject, or to lessening the severity of one or more symptoms of a condition (e.g., susceptibility to bacterial or fungal infections) that may develop in the subject, or any combination thereof. In general, the subject of a preventative regimen will be selected as being an at-risk subject, meaning one that has a profile associated with a risk of contracting HIV that is higher than the relevant baseline population.

"Small molecule" as used herein, is meant to refer to a compound that has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Many pharmaceutical companies have extensive libraries of chemical or biological mixtures comprising arrays of small molecules, often fungal, bacterial, or algal extracts, which can be screened with any of the assays of the invention.

The term "therapeutic index" refers to the therapeutic index of a drug defined as LD50/ED50.

The term "treat," "treating," or "treatment" as used herein means to counteract a medical condition (e.g., a condition related to HIV infection) to the extent that the medical condition is improved according to a clinically acceptable standard (e.g., lower HIV virus count in an infected subject). For example, "to treat an HIV infection" means to improve a subject's ability to resist HIV contraction or inhibit HIV replication in the subject, or to relieve symptoms of a condition related to HIV infection in a patient, wherein the improvement and relief are evaluated using a clinically acceptable standard.

3. BD Agents

The invention provides methods and compositions relating to BD agents, and preferably BD agents having antiviral activity. Preferred embodiments of the invention employ BD agents having antiviral activity against viruses (e.g., HIV) that associate with a chemokine receptor, (e.g., CXCR4).

A BD agent of the invention can be any agent having antiviral activity and having or mimicking one or more structural features of a naturally occurring beta-defensin. A BD-agent may also exhibit a spectrum of antimicrobial activity that is similar to that of a naturally occurring beta-defensin. A BD agent may be a polypeptide, a nucleic acid, a peptidomimetic, or a small molecule.

Wild-type beta defensins have a wide spectrum of antimicrobial activity against Gram-negative and Gram-positive bacteria, fungi, and yeast. Recently, a computational search strategy identified 28 new human beta defensin genes, in addition to the know HBD-1, -2, -3, and -4 genes, in five syntenic chromosomal regions (Schutte et al., Discovery of five conserved beta-defensin gene clusters using a computational search strategy, (2002) Proc Natl Acad Sci USA 99:2129). At least 26 of the predicted genes were found to be transcribed. This study focused on finding β-defensin second exons, the genetic region encoding the mature peptide. It is anticipated that a similar approach could be used to discover all first exon coding sequences and the associated regulatory elements that confer cell specificity and responsiveness to inflammatory stimuli and pathogens. These new findings provide additional candidate BD- and BD like-polypeptides and their encoding nucleic acids, which may also be employed as BD agents of the invention.

Antiviral activity of a BD agent is preferably directed to HIV or a virus utilizing a chemokine receptor such as for example CXCR4 to enter a cell. The antiviral activity of a BD agent may be reflected by 1) the BD agent's ability to bind to a chemokine receptor and optionally to displace binding to the chemokine receptor by its natural ligand, 2) the BD agent's ability to bind to the virion directly, or 3) the BD agent's ability to inhibit the virus from entering a cell. Antiviral activity of a candidate BD agent can be evaluated based on methods described in greater detail below.

Certain embodiments employ a BD agent that comprises a BD-polypeptide. A BD-polypeptide of the invention comprises an amino acid sequence at least 80%, 85%, 90%, 95%, 97%, or 99% identical to the amino acid sequence of a native beta defensin protein, and preferably the amino acid sequence of a mature native beta defensin protein. Preferably, a BD-polypeptide comprises an amino acid sequence at least 80%, 85%, 90%, 95%, 97%, or 99% identical to the amino acid sequence of a mature native BD-2 or BD-3 protein, said BD-polypeptide may be referred to as BD-2 polypeptide or BD-3 polypeptide. Most preferably, a BD-polypeptide comprises an amino acid sequence at least 80%, 85%, 90%, 95%, 97%, or 99% identical to the amino acid sequence of a mature native human BD-2 (HBD-2). or human BD-3 (HBD-3) protein, said BD-polypeptide may be referred to as an HBD-2 polypeptide or HBD-3 polypeptide. A BD agent comprising an HBD-polypeptide may also be referred to as an HBD agent.

In certain embodiments, the methods and compositions disclosed herein may employ, as an HBD-2 agent, an HBD-2 polypeptide comprising an amino acid sequence at least 80%, 85%, 90%, 95%, 97%, or 99% identical to an amino acid sequence selected from the group consisting of: SEQ ID NO:1 and SEQ ID NO:2. In certain embodiments, the HBD-2 agent is a polypeptide obtained by expressing a nucleic acid that is at least 80%, 85%, 90%, 95%, 97%, or 99% identical to a nucleic acid selected from the group consisting of: SEQ ID NOs: 4-7 in a cell. In certain embodiments, the HBD-2 agent is a polypeptide encoded by a nucleic acid that is at least 80%, 85%, 90%, 95%, 97%, or 99% identical to a nucleic acid selected from the group consisting of: SEQ ID NOs:4-7. In certain embodiments, the HBD agent is a polypeptide of SEQ ID NO:1-2 or is encoded by a nucleic acid as set forth in SEQ ID Nos: 4-7. Preferably the HBD-2 agent has a 50% effectiveness at a concentration of about 10 micromolar or less.

In certain embodiments, the methods and compositions disclosed herein may employ, as an HBD-3 agent, a polypeptide comprising an amino acid sequence at least 80%, 85%, 90%, 95%, 97%, or 99% identical to an amino acid sequence selected from the group consisting of: SEQ ID NO:15. In certain embodiments, the HBD-3 agent is a polypeptide obtained by expressing a nucleic acid that is at least 80%, 85%, 90%, 95%, 97%, or 99% identical to a nucleic acid selected from the group consisting of: SEQ ID NOs:16-18 in a cell. In certain embodiments, the HBD-3 agent is a polypeptide encoded by a nucleic acid that is at least 80%, 85%, 90%, 95%, 97%, or 99% identical to a nucleic acid selected from the group consisting of: SEQ ID NOs:16-18. In certain embodiments, the HBD agent is a polypeptide of SEQ ID NO: 15 or is encoded by a nucleic acid as set forth in SEQ ID Nos: 16-18. Preferably the HBD-3 agent has a 50% effectiveness at a concentration of about 10 micromolar or less.

Exemplary HBD2-polypeptide:

```
GIGDPVTCLKSGAICHPVFCPRRYKQIGTCGLPGTKC  (SEQ ID NO:1)
CKKP

MRVLYLLFSFLFIFLMPLPGVFGGIGDPVTCLKSGAI  (SEQ ID NO:2)
CHPVFCPRRYKQIGTCGLPGTKCCKKP
```

Exemplary HBD-3 polypeptide:

```
MRIHYLLFALLFLFLVPVPGHGGIINTLQKYYCRVR  (SEQ ID NO:15)
GGRCAVLSCLPKEEQIGKCSTRGRKCCRRKK
```

The subject BD agents also encompass nucleic acids that encode BD-polypeptides or portions thereof.

In certain aspects the invention involves the use of isolated and/or recombinant nucleic acids encoding BD-polypeptides, such as, for example, SEQ ID NOs: 4-7 and 16-18. Certain methods of the invention are further understood to employ nucleic acids that comprise variants of SEQ ID NOs: 4-7 and 16-18. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 4-7 and 16-18, e.g. due to the degeneracy of the genetic code. For example, nucleic acids encoding HBD-2 polypeptides may be nucleic acids comprising a sequence that is at least 80%, 85%, 90%, 95%, 99% or 100% identical to the sequence of SEQ ID NOs:4-7 or a sequence that encodes the polypeptide of SEQ ID NOs:1 or 2. In other embodiments, variants will also include sequences that will hybridize under highly stringent conditions to a coding sequence of a nucleic acid sequence designated in SEQ ID NOs: 4-7.

```
Exemplary HBD-2 nucleic acid sequence (SEQ ID NO:4)
  1 ctttataagg tggaaggctt gatgtcctcc ccagactcag ctcctggtga agctcccagc 61 catcagccat gagggtcttg tatctcctct tctcgttcct cttcatattc ctgatgcctc
```

-continued

```
 121 ttccaggtga datgggccag ggaaatagga gggttggcca aatggaagaa tggcgtagaa
 181 gttctctgtc tcctctcatt ccctccacc tatctctccc tcatccctct ctctccttcc
 241 tctctctgtg tgtcccctcc atcctttct cctgcttctc tctcttcttc cctctctctc
 301 tttttctgt ctttctttt cctctctccc tagagcatgt ctttctttct ttctctttcc
 361 tttcttctac ccacactttt agactgaatg ccctatttaa ttgaacaaag cattgcttcc
 421 ttcaatagaa aaggagtttg agaacccaat ggacacctca ctcgttcttc taagccaata
 481 tgaaggagcc cagtagcttg taaatatcat ctcttcactg ctttccatgc tacaactgct
 541 gagactatgg ttgaaacctg ttaggtgact ttttaaataa aaggcagaaa ttttgatttt
 601 atctaaagaa agtagtatag aatgtcattt tctaaatttt tatatttaaa gggtagatac
 661 tgcaacctag agaattccag ataatcttaa ggcccagcct atactgtgag aactactgca
 721 gcaagacact ctgcctccag gactttctg atcagaggcc ctgagaacag tccctgccac
 781 taggccactg caggttcaca ggacagggta cagcccattg aaacctactt ttaaacctgg
 841 atgcctaacc ttcattttct ccttgatatt atgaaaataa aataaaaacc atgaaaggat
 901 aaaagaggga gagtggaagg gaaggatgga gaaagggaaa aagaaaattt gagagtaaat
 961 cctaaaacaa ttaatctaat agatatcatc ttgtgaaatc ctcattttac caatcttatt
1021 tatgagtcct gggttttgtg agaacaatgg ggttctgaga ggcaccgag acctcatgtt
1081 ttccaaaacc tagaacagta taatgaagga aggcggggag gcagggaggc agggaggcag
1141 ggaggcaggg aggcgggcag gtggggaggg agggacggaa ggagggaggg agggagggag
1201 ggagggaggg agggataaaa aaagaagaat gaggttgaaa ccaggactta gatattagaa
1261 acaagccatt acaaaattta tttctatggt taattgtggt tttcaactgt aagttacttg
1321 gtgttaattt cctattaaac aatttcagta agttgcatct ttttatccca tctcaggtca
1381 aatacttaac agactaaatg atttgaaaaa gcaaaagttt actggcttgt gtgtgttaaa
1441 atggaggtat ggtggctttg atattatctt cttgtggtgg agctgaattc acaagagatc
1501 gttgctgagc tcctaccaga ccccacctgg aggcccagt cactcaggag agatcagggt
1561 ctttcacaat caggttctac aaaaataaac atcccccaa ccacagcagt gccagtttcc
1621 atgtcagaaa cttagatcca aatgactgac tcgcgtctca ttatcatgat ggaaaagccc
1681 aggcttgaga aagaagcccg ctgcggattt actcaaggcg atactgacac agggtttgtg
1741 ttttccaac atgagttttg agttcttaca cgctgttttgc tcttttttgtg tgttttttcc
1801 ctgttaggtg ttttttggtgg tataggcgat cctgttacct gccttaagag tggagccata
1861 tgtcatccag tcttttgccc tagaaggtat aaacaaattg gcacctgtgg tctccctgga
1921 acaaaatgct gcaaaagcc atgaggaggc caagaagctg ctgtggctga tgcggattca
1981 gaaagggctc cctcatcaga gacgtgcgac atgtaaacca aattaaacta tggtgtccaa
2041 agata
```

Exemplary HBD-2 mRNA (SEQ ID NO:5)
```
   1 ggtgaagctc ccagccatca gccatgaggg tcttgtatct cctcttctcg ttcctcttca
  61 tattcctgat gcctcttcca ggtgtttttg gtggtatagg cgatcctgtt acctgcctta
 121 agagtggagc catatgtcat ccagtctttt gccctagaag gtataaacaa attggcacct
 181 gtggtctccc tggaacaaaa tgctgcaaaa agccatgagg aggccaagaa gctgctgtgg
 241 ctgatgcgga ttcagaaagg gctccctcat cagagacgtg cgacatgtaa accaaattaa
 301 actatggtgt ccaaagata
```

-continued

```
    Exemplary HBD-2 Coding Sequence (Precursor) (SEQ ID NO:6)
  1 atgagggtct tgtatctcct cttctcgttc ctcttcatat tcctgatgcc tcttccaggt 61 gttttggtg  gtataggcga tcctgttacc tgccttaaga gtggagccat atgtcatcca 121 gtcttttgcc ctagaaggta taaacaaatt ggcacctgtg gtctccctgg aacaaaatgc 181 tgcaaaaagc catga Exemplary HBD-2 Coding Sequence (Mature) (SEQ ID NO:7)
  1 ggtataggcg atcctgttac ctgccttaag agtggagcca tatgtcatcc agtcttttgc 61 cctagaaggt ataaacaaat tggcacctgt ggtctccctg aacaaaatg  ctgcaaaaag 121 ccatga Exemplary HBD-3 Coding Sequence (SEQ ID NO:16)
  1 atgaggatcc attatcttct gtttgctttg ctcttcctgt ttttggtgcc tgttccaggt 61 catggaggaa tcataaacac attacagaaa tattattgca gagtcagagg cggccggtgt 121 gctgtgctca gctgccttcc aaaggaggaa cagatcggca agtgctcgac gcgtggccga 181 aaatgctgcc gaagaaagaa ataa Exemplary HBD-3 Gene Sequence (SEQ ID NO:17)
  1 tgagtctcag cgtggggtga agcctagcag ctatgaggat ccattatctt ctgtttgctt 61 tgctcttcct gttttggtg  cctgtcccag gtcatggagg aatcataaac acattacaga 121 aatattattg cagagtcaga ggcggccggt gtgctgtgct cagctgcctt ccaaaggagg 181 aacagatcgg caagtgctcg acgcgtggcc gaaaatgctg ccgaagaaag aaataaaaac 241 cctgaaacat gacgagagtg ttgtaaagtg tggaaatgcc ttcttaaagt ttataaaagt 301 aaaatcaaat tacatttttt tttcaaaaaa aaaaaaa Exemplary HBD-3 mRNA Sequence (SEQ ID NO:18)
  1 catccagtct cagcgtgggg tgaagcctag cagctatgag gatccattat cttctgtttg 61 ctttgctctt cctgttttg  gtgcctgttc caggtcatgg aggaatcata aacacattac 121 agaaatatta ttgcagagtc agaggcggcc ggtgtgctgt gctcagctgc cttccaaagg 181 aggaacagat cggcaagtgc tcgacgcgtg gccgaaaatg ctgccgaaga aagaaataaa 241 aaccctgaaa catgacgaga gtgttg
```

The invention provides a method of identifying a BD agent comprising selecting a candidate agent that can interact with a chemokine receptor, preferably a CXCR4, and optionally further determining whether the selected candidate agent binds HIV virion. Alternatively, a method of identifying a BD agent comprises the step of determining whether the selected candidate agent inhibits HIV entry into a cell. A method of identifying a BD agent comprises the step of determining whether the selected candidate agent has an antiviral or antimicrobial activity similar to that of a native BD-polypeptide.

A method of optimizing a BD agent may further include preparing a composition comprising said BD agent and a pharmaceutically suitable carrier or excipient.

Antimicrobial activity of a candidate BD agent may be evaluated by conventional assays, for example, determining colony formation of a test microbial organism (e.g., a bacterium such as *Staphylococcus aureus*) in the presence or absence of the candidate agent. To illustrate, test organisms can be incubated with or without a candidate BD agent in a suitable buffer, serial dilutions of the incubation mixture can be plated, and then colonies formed on the plates can be counted to determine whether the candidate BD agent has any effect on the test organisms' ability to form colonies. By changing the concentration of the candidate BD agent in the assay, the effectiveness of the agent's antimicrobial activity can also be determined. See also Yamaguchi et al., Journal of Immunology (2002) 2516-23 and Harder et al., Journal of Biol. Chem. (2001) 276:5707-13, hereby incorporated by reference in their entirety.

Antiviral activity of a candidate BD agent may be evaluated by assays known in the art. For example, infectivity of a virus may be determined by reverse transcriptase assays using the cell-free supernatants from cells exposed to the virus. See, e.g., Quinones-Mateu et al., Journal of Virol. (2000) 74:9222-33. An exemplary assay to determine a BD agent's anti-HIV activity is set forth as follows: HIV may be incubated with or without a candidate BD agent; the incubation may be conducted with different concentrations of the candidate BD agent to determine the agent's anti-HIV effectiveness. The HIV-agent mixtures may then be used to infect cells, e.g., peripheral blood mononuclear cells (PBMC), MT-4 and CEM X4/R5 T-cells. After a suitable time (e.g., 2 hours at 37° C.) of incubation, the cells may be cultured further (e.g., for 48 hours), and cell-free supernatants from these cultured cells can then be used to monitor infectivity by a reverse transcriptase assay. It will be obvious to a skilled artisan to modify the conditions and other variables of the exemplary assay. For example, HIV, a candidate BD agent, and the cells may be incubated together without preincubation of the HIV and the agent; the time length of incubation may also be modified.

A candidate BD agent's anti-HIV activity may also be evaluated based on its ability to interact with a chemokine receptor. By "interact with a chemokine receptor" herein is meant binding to a chemokine receptor or causing internalization of a chemokine receptor. While not wishing to bound by a particular theory, binding of a BD agent to a chemokine receptor may cause internalization of the chemokine receptor thus reducing cell surface expression of the chemokine receptor.

A candidate BD agent's ability to bind a chemokine receptor may be evaluated using a cell-free assay or cell-based assay (see Example 5). A fragment of the chemokine receptor (e.g., extracellular domain) responsible for binding may be used in a binding assay to screen for BD agents. Competitive binding assays may also be employed using a chemokine receptor's natural ligand (e.g., stromal cell derived factor 1 (SDF-1) for CXCR4) and a candidate BD agent.

A candidate BD agent's ability to interact with a chemokine receptor may be evaluated using a cell-based assay to determine cell surface expression of the chemokine receptor when exposed to the candidate BD agent. Example 5 illustrates a method of determining whether a BD agent can downmodulate cell surface expression of a chemokine receptor.

A candidate BD agent's anti-HIV activity may also be evaluated based on its ability to interact with HIV virions. A candidate BD agent's ability to interaction with HIV virions may be evaluated using a binding assay mixture comprising the candidate BD agent and virions. Example 6 illustrates a binding assay and a method to determine whether a BD agent binds to an HIV virion.

Generally, BD agents which can bind with molecules related to the viral infection process (e.g., a chemokine receptor, a fragment of a chemokine receptor, or a virion) may be identified by reacting one of the molecules with a test agent which potentially binds to the molecule, under conditions which permit binding of the molecule and test agent, and detecting binding. Binding may be detected by assaying for agent-molecule conjugates, for free agent, or for non-complexed molecules, or other alteration of the molecule (e.g., internalization of a chemokine receptor). Conditions which permit the formation of agent-molecule conjugates may be selected having regard to factors such as the nature and amounts of the agent and the molecule.

The agent-molecule conjugate, free agent or non-complexed molecules may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the molecule or the agent, or labeled molecule, or a labeled agent may be utilized. The antibodies, proteins, or agents may be labeled with a detectable substance, such as radiolabeling or fluorescent labeling.

A molecule, or complex of the invention, or the agent used in the method of the invention may be rendered insoluble. For example, a molecule, or agent may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insoluble molecule or agent may be prepared by reacting the material with a suitable insoluble carrier using known chemical or physical methods, for example, cyanogen bromide coupling.

As will be apparent to a skilled artisan, the assays described herein are adaptable to a high-throughput format in screening for various agents of the invention.

Multivalent agents may also be identified using the binding assays described above. For example, a BD agent may be bivalent, in that it has at least two binding sites on its target molecule, e.g., a chemokine receptor or an HIV virion. A bivalent BD agent may also bind to both a chemokine receptor and an HIV virion.

Variant BD agents may be prepared from the known BD agents, e.g., HBD-2 or HBD-3 polypeptides or nucleic acids, according to the methods described in greater detail below.

4. BD-Inducing Agents

In certain aspects, the invention provides methods and compositions relating to BD-inducing agents, and preferably BD-inducing agents having antiviral activity.

By "BD-inducing agent" is meant an agent that induces or increases expression of a BD-polypeptide in a cell. Preferably, a BD-inducing agent induces or increases expression of an HBD-2 polypeptide or HBD-3 polypeptide in a human cell; such a BD-inducing agent may also be referred to as HBD-inducing agent. Expression of a BD-polypeptide can be determined by known methods such as measuring mRNA level or protein level, as described in greater detail below. By "induces or increases" is meant that (a) a BD-polypeptide is expressed in the presence of a BD-inducing agent whereas the BD-polypeptide is not detectably expressed in the absence of the BD-inducing agent or (b) expression of BD-polypeptide in the presence of a BD-inducing agent is greater (e.g., by 1, 2, 5, 10, 20, 100, 1000, 10000 fold) than that in the absence of the BD-inducing agent.

A BD-inducing agent may be essentially any composition, including, for example, one or more polypeptides (including portions thereof or a fusion protein), small molecules, peptidomimetics, nucleic acids, or mixtures thereof.

Certain small molecules were known to induce epithelial beta defensin expression. For example, isoleucine-1 and its analogs can activate transcription of epithelial beta defensin genes and the transcriptional activation appears to involve the NF-kappaB/rel family of trans-activating factors. High calcium concentration (1.7 mM) alone applied in culture medium also appears sufficient to induce HBD-2 and HBD-3 mRNA expression in epidermal cells. As shown in Example 2 and FIG. 3 herein, phorbol myristate acetate also induces HBD-2 and HBD-3, but not HBD-1, mRNA expression in normal human oral epithelium and cells. The invention contemplates using these known small molecules as BD-inducing agents and their mechanisms (e.g., high calcium, or activating NF-kappaB/rel) may be used to guide development of BD-inducing agents. The invention further contemplates screening small molecule libraries as described in greater details below to identify and optimize a BD-inducing agent.

In certain embodiments, the BD-inducing agent induces a HBD-2 or HBD-3. In yet other embodiments, the BD-inducing agent induces a polypeptide comprising an amino acid sequence at least 80%, 85%, 90%, 95%, 97%, or 98-99% identical to an amino acid sequence selected from the group consisting of: SEQ ID NO:1 and SEQ ID NO:2. In certain embodiments, the BD-inducing agent induces a polypeptide obtained by expressing a nucleic acid that is at least 80%, 85%, 90%, 95%, 97%, or 98-99% identical to a nucleic acid selected from the group consisting of: SEQ ID NOs: 4-7 in a cell. In certain embodiments, the BD-inducing agent induces a polypeptide encoded by a nucleic acid that is at least 80%, 85%, 90%, 95%, 97%, or 98-99% identical to a nucleic acid selected from the group consisting of: SEQ ID NOs:4-7.

In yet other embodiments, a BD-inducing agent induces a polypeptide comprising an amino acid sequence at least 80%, 85%, 90%, 95%, 97%, or 98-99% identical to an amino acid sequence of: SEQ ID NO:15. In certain embodiments, a BD-inducing agent induces a polypeptide obtained by expressing a nucleic acid that is at least 80%, 85%, 90%, 95%, 97%, or 98-99% identical to a nucleic acid selected from the group consisting of: SEQ ID NOs:16-18 in a cell. In certain embodiments, a BD-inducing agent induces a polypeptide encoded by a nucleic acid that is at least 80%, 85%, 90%, 95%, 97%, or 98-99% identical to a nucleic acid selected from the group consisting of: SEQ ID NOs:16-18.

In certain embodiments, the methods and compositions disclosed herein may employ, as an BD-inducing agent, a FAD-I polypeptide. In certain embodiments, an FAD-I polypeptide is a polypeptide comprising an amino acid sequence at least 80%, 85%, 90%, 95%, 97%, or 98-99% identical to an amino acid sequence of SEQ ID NO: 3, 9, 11, or 13. In certain embodiments, an FAD-I polypeptide is a polypeptide obtained by expressing a nucleic acid that is at least 80%, 85%, 90%, 95%, 97%, or 98-99% identical to a nucleic acid of SEQ ID NO:8, 10, 12, or 14 in a cell. In certain embodiments, a FAD-I polypeptide is a polypeptide encoded by a nucleic acid that is at least 80%, 85%, 90%, 95%, 97%, or 98-99% identical to a nucleic acid of SEQ ID NO:8, 10, 12, or 14.

In certain embodiments, the methods and compositions disclosed herein may employ, as an BD-inducing agent, a viral protein. In certain embodiments, the viral protein is an HIV protein such as for example gp120 or gp41. In certain embodiments, an HIV protein is a polypeptide comprising an amino acid sequence at least 80%, 85%, 90%, 95%, 97%, or 98-99% identical to an amino acid sequence of SEQ ID NO:19, 20, or 21. In certain embodiments, an HIV protein is a polypeptide obtained by expressing a nucleic acid that is at least 80%, 85%, 90%, 95%, 97%, or 98-99% identical to a nucleic acid of SEQ ID NO:19, 20, or 21 in a cell. In certain embodiments, an HIV protein is a polypeptide encoded by a nucleic acid that is at least 80%, 85%, 90%, 95%, 97%, or 98-99% identical to a nucleic acid of SEQ ID NO: 19, 20, or 21.

Exemplary BD-Inducing Agents:

```
SEQ ID NO.:3 (NP_602592)
MSLFLVACGEKKEEEKPAEQAAVEATATEAPATETTEAAAEAKTFSLKTEDGKEFTLVV

AADGSTATLTDAEGKATELKNAETASGERYADEAGNEVAMKGAEGILTLGDLKEVPVT

VEAK

SEQ ID NO.:9 (NP_602354)
MKKILLLLSSLFLFACANIDTGVDESKEAQISRLLKEADKKKEKTVEVEKKLVTDNGEEV

IEEEATVQNKKSHKGMTRGEIMEYEMTRVSDEMNALQADVQQYQEKKAQLKAYQEKL

QKLEELNNAGIK

SEQ ID NO.:11 (NP_602356)
MKKVILTLFVLLSIGIFANDEIISELKGLNAEYENLVKEEEARFQKEKELSERAAAQNVKL

AELKASIEEKLLAAPEERKTKFFKDTFDGLVKDYSKYLSQINEKIAENTEIVSNFEKIQKIR

SEQ ID NO.:13 (NP_603171)
MKKFLLLAVLAVSASAFAANDAASLVGELQALDAEYQNLANQEEARFNEERAQADAA

RQALAQNEQVYNELSQRAQRLQAEANTRFYKSQYQDLASKYEDALKKLESEMEQQKA

IISDFEKIQALRAGN

SEQ ID NO:19 (NP_057856.1)
   1 mrvkekyqhl wrwgwrwgtm llgmlmicsa teklwvtvyy gvpvwkeatt tlfcasdaka 61 ydtevhnvwa thacvptdpn pqevvlvnvt enfnmwkndm veqmhediis lwdqslkpcv 121 kltplcvslk ctdlkndtnt nsssgrmime kgeikncsfn iststsirgkvq keyaffykld 181 iipidndtts ykltscntsv itqacpkvsf epipihycap agfailkcnn ktfngtgpct 241 nvstvqcthg irpvvstqll lngslaeeev virsvnftdn aktiivqlnt sveinctrpn 301 nntrkririq rgpgrafvti gkignmrqah cnisrakwnn tlkqiasklr eqfgnnktii 361 fkqssggdpe ivthsfncgg effycnstql fnstwfnstw stegsnnteg sdtitlpcri 421 kqiinmwqkv gkamyappis gqircssnit gllltrdggn snneseifrp gggdmrdnwr 481 selykykvvk ieplgvaptk akrrvvqrek ravgigalfl gflgaagstm gaasmtltvq 541 arqllsgivq qqnnllraie aqqhllqltv wgikqlqari laverylkdq qllgiwgcsg 601 klicttavpw naswsnksle qiwnhttwme wdreinnyts lihslieesq nqqekneqel 661 leldkwaslw nwfnitnwlw yiklfimivg glvglrivfa vlsivnrvrq gysplsfqth 721 lptprgpdrp egieeegger drdrsirlvn gslaliwddl rslclfsyhr lrdllllivtr
```

-continued

```
781ivellgrrgw ealkywwnll qywsqelkns avsllnatai avaegtdrvi evvqgacrai

841rhiprrirqg lerill

SEQ ID NO:20 (amino acids 29-511, mature peptide, of HIV-1 gp120)
   sa teklwvtvyy gvpvwkeatt tlfcasdaka ydtevhnvwa thacvptdpn pqevvlvnvt enfnmwkndm veqmhediis lwdqslkpcv kltplcvslk ctdlkndtnt nsssgrmime kgeikncsfn istsirgkvq keyaffykld iipidndtts ykltscntsv itqacpkvsf epipihycap agfailkcnn ktfngtgpct nvstvqcthg irpvvstqll lngslaeeev virsvnftdn aktiivqlnt sveinctrpn nntrkririq rgpgrafvti gkignmrqah cnisrakwnn tlkqiasklr eqfgnnktii fkqssggdpe ivthsfncgg effycnstql fnstwfnstw stegsnnteg sdtitlpcri kqiinmwqkv gkamyappis gqircssnit glllltrdggn snneseifrp gggdmrdnwr selykykvvk ieplgvaptk akrrvvqrek r SEQ ID NO:21 (amino acids 512-856, mature peptide, HIV gp41)
512avgigalfl gflgaagstm gaasmtltvq 541arqllsgivq qqnnllraie aqqhllqltv wgikqlqari laverylkdq qllgiwgcsg 601klicttavpw naswsnksle qiwnhttwme wdreinnyts lihslieesq nqqekneqel 661leldkwaslw nwfnitnwlw yiklfimivg glvglrivfa vlsivnrvrq gysplsfqth 721lptprgpdrp egieeegger drdrsirlvn gslaliwddl rslclfsyhr lrdlllivtr 781ivellgrrgw ealkywwnll qywsqelkns avsllnatai avaegtdrvi evvqgacrai 841rhiprrirqg lerill
```

Various cell lines can be utilized for screening of the candidate BD-inducing agents, e.g., normal human oral epithelial cells. Candidate agents can be screened for their ability to induce in the cells expression of a BD gene such as for example a BD-2 or BD-3. Expression of a BD gene can be determined and measured by level of mRNA transcribed from the BD gene, level of protein translated from the mRNA, or level of mature protein processed from the translated protein. Thus, a BD-inducing agent may induce or increase expression of a BD-polypeptide by activate transcription of the BD gene encoding the BD-polypeptide. Alternatively, a BD-inducing agent may facilitate translation from a BD mRNA. Yet another alternative BD-inducing agent may enhance processing of a translated product of BD gene and thereby increase production of the mature BD-polypeptide.

Conventional methods may be employed or modified to determine mRNA level or protein level. To illustrate, Example 1 describes a method of real-time RT-PCR assay to quantify HBD mRNA. Antibodies to a BD-polypeptide may be used to determine protein level. The BD expressed may be endogenous to the cells utilized in the assays, for example the normal human oral epithelial cells. As is known in the art, cell lines can also be created via transfections with nucleic acids encoding the proteins (e.g., an HBD-2 or HBD-3 polypeptide) desired to be present for a subject assay.

Alternatively, expression of a BD gene may also be measured by determining the activity of a promoter responsible for expression of a native BD gene, which may also be referred to as a BD-promoter. A "promoter" is a control or regulatory sequence that is a region of a nucleic acid sequence at which initiation and rate of transcription are controlled. It may contain genetic elements at which regulatory proteins and molecules may bind such as RNA polymerase and other transcription factors. A BD-promoter is a control or regulatory sequence that is responsible for expression of a BD gene in a cell. A BD-promoter may comprise a nucleic acid sequence that can interaction with transcriptional activators. For example, the BD-promoter is speculated to be responsive to NF-kappaB/rel family of trans-activating factors. A promoter may or may not be used in conjunction with an "enhancer," which refers to a cis-acting regulatory sequence involved in the transcriptional activation of a nucleic acid sequence.

Promoter activity can also be determined using conventional methods such as reporter gene assays in which reporter genes are operably linked to a promoter of interest. The phrase "operably linked" means that a promoter is in a correct functional location and/or orientation in relation to a nucleic acid sequence to control transcriptional initiation and/or expression of that sequence.

Various reporter gene constructs may be used in accord with the methods of the invention and include, for example, reporter genes which produce such detectable signals as selected from the group consisting of an enzymatic signal, a fluorescent signal, a phosphorescent signal and drug resistance. To illustrate, cells may be transfected with a BD-2 or BD-3 reporter gene construct, wherein a BD-promoter or potential BD-inducing agent responsive regulatory element of a BD-2 or BD-3 gene is operably linked to a reporter gene, and preferably a reporter gene that produces a fluorescent protein (e.g. green fluorescent protein) or an enzyme that can generate a fluorescent substrate or other detectable signal. The cells are then contacted with a candidate BD-inducing agent and reporter gene expression is assessed. In certain embodiments, an assay may comprise employing a cell that naturally has inducible BD-2 or BD-3 expression, such as a normal human oral epithelial cell. Alternatively, the cells may be transfected with a reporter gene construct.

5. Agents that Potentiate the Interaction Between a BD-Polypeptide and a Chemokine Receptor In certain aspects, the invention provides methods and compositions relating to agents that potentiate the interaction between a BD-polypeptide and a chemokine receptor, preferably CXCR4. Such an agent may be a polypeptide, a nucleic acid, a peptidomimetic, or a small molecule, but will preferably be an antibody selected for this property. In preferred embodiments, an agent of the invention potentiates the interaction between a BD-polypeptide and CXCR4. The BD-polypeptide is preferably a HBD-polypeptide. In certain embodiments, an agent of the invention potentiates the interaction between a HBD-2 polypeptide and CXCR4. In certain embodiments, an agent of the invention potentiates the interaction between a HBD-3 polypeptide and CXCR4. The same agent may potentiate the interactions between CXCR4 and HBD-2 polypeptide and between CXCR4 and HBD-3 polypeptide.

Assays for evaluating the interaction between a BD agent and a chemokine receptor as described above may be employed and modified to screen for and optimize an agent that can potentiate the interaction between a BD-polypeptide and a chemokine receptor.

The invention contemplates a method for evaluating a compound for its ability to modulate a complex of the invention, by assaying for an agonist or antagonist of the binding of the molecules in the complex. A complex of the invention may comprise a BD-polypeptide and a chemokine receptor. Preferred embodiments employ a complex comprising a HBD-polypeptide and CXCR4 or fragments thereof, and the HBD-polypeptide can be a HBD-2 or HBD-3 polypeptide. A basic method for evaluating if a compound is an agonist or antagonist of the binding of molecules in a complex of the invention, is to prepare a reaction or assay mixture containing the molecules and the test compound under conditions which permit the molecules to bind and form a complex. The test compound may be initially added to the mixture, or may be added subsequent to the addition of molecules. Control reaction mixtures without the test compound or with a placebo are also prepared. The formation of complexes is detected and the formation of complexes in the control reaction but not in the reaction mixture indicates that the test compound interferes with the interaction of the molecules. Increased complex formation relative to a control reaction indicates that the test compound potentiates the interaction of the molecules. The reactions may be carried out in the liquid phase or the molecules, or test compound may be immobilized as described herein.

The invention also contemplates using a cell-based assay to evaluate a compound's effect on a complex of the invention. For example, a two-hybrid assay system may be adapted to express a complex of the invention formed by fragments of CXCR4 and a BD-polypeptide. Such an assay system, as well as other assays described herein, is adaptable to a high-throughput format to evaluate a large number of test compounds.

It will be understood that the agonists and antagonists that can be assayed using the methods of the invention may act on one or more of the binding sites on the interacting molecules in the complex including agonist binding sites, competitive antagonist binding sites, non-competitive antagonist binding sites or allosteric sites.

The invention also makes it possible to screen for antagonists that inhibit or agonists that further enhance the effects of an agonist of the interaction of molecules in a complex of the invention. Thus, the invention may be used to assay for a compound that competes for the same binding site of a molecule in a complex of the invention.

The invention also contemplates methods for identifying novel compounds that modulate protein-protein interactions responsible for forming a complex of the invention. Protein-protein interactions may be identified using conventional methods such as co-immunoprecipitation, crosslinking and co-purification through gradients or chromatographic columns. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, a quadrupole/time-of-flight hybrid instrument (QqTOF) may be used. These methods of detecting protein-protein interactions can be readily modified to evaluate a compound's effect on the detected protein-protein interactions. BIAcore Biosensor is also a well-known system to measure interactions between macromolecules, and can be useful to evaluate a test compound's effectiveness in modulating interactions between molecules of a complex of the invention.

It will be appreciated that fragments, fusion proteins, and recombinant fusion proteins may be used in the above-described methods. It will also be appreciated that the complexes of the invention may be reconstituted in vitro using recombinant molecules and the effect of a test substance may be evaluated in the reconstituted system.

The reagents suitable for applying the methods of the invention to evaluate substances and compounds may be packaged into convenient kits providing the necessary materials packaged into suitable containers. The kits may also include suitable supports useful in performing the methods of the invention.

6. Agents that Potentiate the Interaction Between a BD-Polypeptide and a Virion

The invention also provides an agent and methods thereof that can potentiate the interaction between a BD-polypeptide and a virion. In preferred embodiments, an agent of the invention potentiates the interaction between a BD-polypeptide and an HIV virion.

Assays for evaluating the interaction between a BD agent and a virion as described above may be employed and modified to screen for and optimize an agent that can potentiate the interaction between a BD-polypeptide and a virion.

Assays described above for evaluating and optimizing an agent or a compound that can potentiate the interaction between a BD-polypeptide and a chemokine receptor can be readily modified to evaluate and optimize an agent that can potentiate the interaction between a BD-polypeptide and a virion. In the modified assays, a complex of the invention is formed by a BD-polypeptide and a virion. Preferred embodiments employ complexes formed by a HBD-2 or HBD-3 polypeptide or fragments thereof and an HIV virion.

7. Variations

A variety of polypeptide agents are described herein, including naturally occurring beta-defensin and beta-defensin-inducing polypeptides. Variants of such polypeptides may be readily prepared and tested for activity. An example of variant agents of the invention may be variant polypeptides, e.g., a BD-polypeptide or a FAD-I polypeptide having a modification that enhances the modified polypeptide's stability or other properties. Another example of variant agents of the invention may be created through making peptidomimetics based on, e.g., a BD-polypeptide or a FAD-I polypeptide. Yet another example of variant agents of the invention may be variant nucleic acids, e.g., a nucleic acid having a modification or mutation that enhances the modified or mutated nucleic acid's uses in, e.g., making recombinant proteins or gene therapy.

Variant agents of the invention may be evaluated by the methods described herein. For example, variant BD agents may be evaluated for their antimicrobial or antiviral effectiveness. Variant BD-inducing agents may also be evaluated for their ability to induce expression of a BD-polypeptide or a reporter gene operably linked to a promoter responsible for expression of a BD gene. Other variant agents may also be assayed for their effect on the interaction between a BD-polypeptide and a chemokine receptor or an HIV virion.

In certain embodiments, small molecules are candidate agents to be screened to identify an agent of the invention. In certain preferred embodiments, small molecules are generated by combinatorial synthesis.

The candidate agents used in the invention may be pharmacologic agents already known in the art or may be agents previously unknown to have any pharmacological activity. The agents may be naturally arising or designed or prepared in the laboratory. They may be isolated from microorganisms, animals, or plants, or may be produced recombinantly, or synthesized by chemical methods known in the art. In some embodiments, candidate agents are identified from small chemical libraries, peptide libraries, or collections of natural products using the methods of the present invention. Tan et al. described a library with over two million synthetic compounds that is compatible with miniaturized cell-based assays (J. Am. Chem. Soc. 120, 8565-8566, 1998). It is within the scope of the present invention that such a library may be used to screen for agents that are BD agents, BD-inducing agents, or other agents of the invention. There are numerous commercially available compound libraries, such as the Chembridge DIVERSet. Libraries are also available from academic investigators, such as the Diversity set from the NCI developmental therapeutics program.

One basic approach to search for a subject agent is screening of compound libraries. One may simply acquire, from various commercial sources, small molecule libraries that are believed to meet the basic criteria for useful drugs in an effort to identify useful compounds by "brute force." Screening of such libraries, including combinatorially generated libraries, is a rapid and efficient way to screen a large number of related (and unrelated) compounds for activity.

Combinatorial approaches also lend themselves to rapid evolution of potential drugs by the creation of second, third, and fourth generation variant compounds modeled on active but otherwise undesirable compounds. It will be understood that undesirable compounds include compounds that are typically toxic, but have been modified to reduce the toxicity or compounds that typically have little effect with minimal toxicity and are used in combination with another compound to produce the desired effect.

The invention also provides mimetics, e.g., peptide or non-peptide agents, which are able to mimic action of the authentic protein, e.g., an HBD-2, an HBD-3, or a FAD-I, in a host. Such mutagenic techniques as described herein, as well as the thioredoxin system, are also particularly useful for mapping the determinants which participate in protein-protein interactions of interest. For example, amino acid residues of a BD-polypeptide may be mapped to determine which ones affect the BD-polypeptide's activity, e.g., antimicrobial or antiviral effectiveness, interaction with a chemokine receptor or an HIV virion. To illustrate, the critical residues of a BD-polypeptide such as for example an HBD-2 or HBD-3 polypeptide can be determined and used to generate its derived peptidomimetics which can affect the binding between the HBD-2 or HBD-3 polypeptide with another molecule such as the CXCR4 receptor protein or an HIV virion. By employing, for example, scanning mutagenesis to map the amino acid residues of a BD-polypeptide which are involved in interacting to another molecule such as CXCR4 or an HIV virion, peptidomimetic compounds can be generated which mimic those residues involved in the interactions of interest. In other aspects, the critical residues of a BD-inducing polypeptide can be determined with which can induce expression of a BD-polypeptide. Non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewensbn et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

Many useful pharmacological compounds are compounds structurally related to compounds that interact naturally with the target, e.g., a BD-polypeptide, a CXCR4, an HIV virion, a promoter responsible for driving expression of a beta defensin in cells, the binding interface between a BD-polypeptide and a CXCR4 or an HIV virion. Creating and examining the action of such molecules is known as "rational drug design," and include making predictions relating to the structure of the targets. Thus, it is understood that a subject agent identified by the present invention may be a small molecule or any other compound (e.g., polypeptide or polynucleotide) that may be designed through rational drug design starting from known binders of the targets.

The goal of rational drug design is to produce structural analogs of biologically active target compounds. By creating such analogs, it is possible to fashion drugs that are more active or stable than the natural or earlier generation molecules, have different susceptibility to alteration or may affect the function of various other molecules. In one approach, one can generate a three-dimensional structure for molecules like the targets, and then design a molecule for its ability to interact with the targets. This could be accomplished by X-ray crystallography, computer modeling, or by a combination of both approaches.

Certain embodiments of the invention employ polypeptides, e.g., a BD agent comprising a BD-polypeptide, or a BD-inducing agent comprising a FAD-I polypeptide. Variant polypeptides may be derived from a polypeptide of the invention, e.g., a full-length HBD-2 or HBD-3 polypeptide, or a FAD-I polypeptide. Isolated peptidyl portions of the subject polypeptides can be obtained by screening polypeptides recombinantly produced from the corresponding fragment of the nucleic acids encoding such polypeptides. In addition, fragments can be chemically synthesized using techniques known in the art such as conventional Merrifield solid phase f-Moc or t-Boc chemistry. For example, any one of the subject polypeptides can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as an agent of the invention.

It is also possible to modify the structure of a subject polypeptide for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the subject polypeptide. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of BD-inducing, FAD-I polypeptide can be assessed, e.g., for their ability induce BD-2 or BD-3 production in a cell. Such variant forms of a BD-polypeptide can be assessed, e.g., for their ability to inhibit HIV infection of cells or to kill certain bacteria or inhibit colony formation of certain bacteria such as S. aureus. Polypeptides in which more than one replacement has taken place can readily be tested in the same manner.

This invention further contemplates a method of generating sets of combinatorial mutants of the subject polypeptides (e.g., a BD-polypeptide or a BD-inducing polypeptide such as FAD-I) as well as truncation mutants. The purpose of screening such combinatorial libraries is to generate, for example, variants or homologs which can act as either agonists or antagonist, or alternatively, which possess novel activities all together. Combinatorially-derived variants or homologs can be generated which have a selective potency relative to a naturally occurring subject polypeptide. Such proteins, when expressed from recombinant DNA constructs, can be used in, e.g., gene therapy protocols.

Likewise, mutagenesis can give rise to variants which have intracellular half-lives dramatically different than the corresponding wild-type protein. For example, the variant protein can be rendered either more stable or less stable to proteolytic degradation or other cellular process which result in destruction of, or otherwise inactivation of the polypeptide of interest.

In similar fashion, variants or homologs can be generated by the present combinatorial approach to act as antagonists, in that they are able to interfere with the ability of the corresponding wild-type protein to function.

In a representative embodiment, the amino acid sequences for a population of BD-polypeptides or BD-inducing polypeptides are aligned, preferably to promote the highest homology possible. Such a population of variants can include, for example, various beta defensins from different species, homologs from one or more species of Fusobacterium, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential sequence that has function similar to a naturally occurring subject polypeptide (e.g., a BD-polypeptide or a FAD-I). For instance, a mixture of synthetic oligonucleotides can be enzymatically ligated into gene sequences such that the degenerate set of potential beta defensin nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos: 5,223,409, 5,198,346, and 5,096,815). Alternatively, other forms of mutagenesis can be utilized to generate a combinatorial library. For example, BD or BD-inducing variant agents can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.;

and Greener et al., (1994) Strategies in Mol Biol 7:32-34). Linker scanning mutagenesis, particularly in a combinatorial setting, is an attractive method for identifying truncated and bioactive variants of BD- or BD-inducing polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Polypeptides of the invention may further comprise post-translational or non-amino acid elements, such as hydrophobic modifications (e.g. polyethylene glycols or lipids), poly- or mono-saccharide modifications, phosphates, acetylations, etc. Effects of such elements on the functionality of a polypeptide may be tested as described herein.

Polypeptides of the invention may also comprise (fusion or chimeric) polypeptides. Fusion polypeptides may be useful for making recombinant polypeptides of the invention. Alternatively, fusion polypeptides may have enhanced stability or functionality which can be tested as described herein. An exemplary fusion polypeptide may be a bivalent BD agent which comprises a fragment that interacts with a chemokine receptor and another fragment that binds to an HIV virion.

8. Pharmaceutical Composition and Preparations

Pharmaceutical compositions for use in accordance with the present invention may be formulated in conventional manner using one or more physiologically acceptable carriers or excipients. In certain aspects, the application provides compositions comprising an agent of the invention and an excipient that is a pharmaceutically acceptable carrier. Such compositions may be designed for delivery systemically or locally, and may be formulated for administration in any convenient way for use in human or veterinary medicine. In certain embodiments, the composition is formulated for local delivery to a particular epithelium, optionally a mucosal epithelium. For example, a composition may be formulated for delivery to the mouth, the eye, the skin, the vagina, the rectum, the intestines and the nose or other airways. In certain embodiments, the application provides methods for making a medicament comprising an agent of the invention and an excipient for the administration by one of the above-described modes.

Thus, another aspect of the present invention provides compositions, optionally pharmaceutically acceptable compositions, comprising an amount, optionally a therapeutically-effective amount, of one or more of the agents or compositions described above, formulated together with one or more excipients, including additives and/or diluents. As described in detail below, the compositions may be specially formulated for administration in solid or liquid form, including those adapted for the following: (1) systemic or local oral administration, for example, drenches (aqueous or non-aqueous solutions or suspensions), tablets, boluses, powders, granules, pastes for application to the tongue, toothpastes or mouthwashes, films or strips (e.g., Listerine PocketPaks® Strip, which is a micro-thin starch-based film impregnated with ingredients); (2) parenteral administration, for example, by subcutaneous, intramuscular or intravenous injection as, for example, a sterile solution or suspension; (3) topical application, for example, as a cream, ointment or spray applied to the skin or mucous membrane; or (4) intravaginally or intrarectally, for example, as a pessary, cream, foam, or film that dissolves (e.g., the type of film used in vaginal contraceptive Films). However, in certain embodiments an agent or composition of the invention may be simply dissolved or suspended in sterile water.

The phrase "therapeutically-effective amount" as used herein means that amount of a compound, material, or composition comprising an agent or composition of the present invention which is effective for producing some desired therapeutic effect by, for example, increasing BD-polypeptide production or inhibiting HIV entry in at least a subpopulation of cells in an animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "excipient" as used herein means a material, composition or vehicle, such as a liquid or solid filler, diluent, excipient, solvent or encapsulating material, optionally pharmaceutically-acceptable, involved in administering the subject BD or BD-inducing polypeptide. Each excipient should be compatible with the other ingredients of the formulation and not injurious to the subject. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compositions may also include excipients that are salts, preferably relatively non-toxic, inorganic and organic acid salts. These salts can be prepared in situ during the final isolation and purification of the agents or compositions of the disclosure, or by separately reacting a purified agent or composition with a suitable organic or inorganic acid, and isolating the salt thus formed. Representative salts include the chloride, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19). Other salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents or compositions of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent or composition of the present invention with the carrier and, optionally, one or more accessory ingredients. In general, the formulations are prepared by uniformly and intimately bringing into association an agent or composition of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as tooth pastes or mouth washes and the like, each containing a predetermined amount of an agent or composition of the present invention as an active ingredient. An agent or composition of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the agents or compositions of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds (e.g., agents or compositions of the invention), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more agents or compositions of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the FAD-I polypeptide.

Formulations of the present invention which are suitable for vaginal administration also include pessaries, tampons, creams, gels, pastes, foams or spray formulations containing such carriers as are known in the art to be appropriate. Dosage forms for the topical or transdermal (systemic) or dermal (local) administration of an agent or composition of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent or composition of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye drops, ointments, powders, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the agents or compositions of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition". W. H. Freedman and CO., San Francisco, U.S.A., 1969 or "Livestock Feeds and Feeding" O and B books. Corvallis, Oreg., U.S.A., 1977).

An agent of the invention may be incorporated into contraceptives, such as condoms, female condoms, spermicidal ointment, contraceptive films or sponges and the like.

In yet another embodiment, the BD or BD-inducing agent can be administered as part of a combinatorial therapy with other agents. For example, the combinatorial therapy can include a BD or BD-inducing agent with at least one antibacterial, antiviral or antifungal agent. In a preferred embodiment, a BD or BD-inducing agent is administered with one or more additional antiviral agents such as: a reverse transcriptase inhibitor, such as a nucleoside analog, e.g. Zidovudine, Didanosine, Zalcitabine, Stavudine, Lamivudine, and non-nucleoside analogs, e.g. Nevirapine, Delavirdine, or a protease inhibitor such as Saquinavir, Ritonavir, Indinavir and Nelfinavir. Others will be, in view of this disclosure, known to those of skill in the art.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the agents of the invention are formulated into ointments, salves, gels, or creams as generally known in the art.

In certain aspects, the invention provides transdermal patches to deliver an agent to a subject. By "transdermal patch" is meant a system capable of delivery of a drug to a subject via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the subject patient. On contact with the skin, the drug-retaining matrix delivers drug to the skin, the drug then passing through the skin into the patient's system.

Agents of the invention may be combined to formulate a pharmaceutical composition. A desirable combination would be a first agent selected from a BD agent or BD-inducing agent and a second agent selected from an agent that potentiates the interaction between a BD-polypeptide and a chemokine receptor or an agent that potentiates the interaction between a BD-polypeptide and a virion (e.g., an HIV virion).

An agent of the invention may also be combined with another antimicrobial or antiviral agent to formulate a pharmaceutical composition or a pharmaceutical package.

9. Methods of Use

In certain aspects, the application relates to method for treating a viral infection (e.g., HIV infection) in a subject, the method comprising administering to the subject an effective amount of an agent selected from the group consisting of: a BD agent; a BD-inducing agent; an agent that potentiates the interaction between a BD-polypeptide and a chemokine receptor; and an agent that potentiates the interaction between a BD-polypeptide and the virus.

In certain aspects the application relates to a method for inhibiting or preventing the contraction of a virus (e.g., HIV) in a subject, the method comprising administering to the subject an effective amount of an agent selected from the group consisting of: an BD agent; BD-inducing agent; an agent that potentiates the interaction between a BD-polypeptide and a chemokine receptor; and an agent that potentiates the interaction between a BD-polypeptide and the virus. In general, such methods will be applied to subjects that are identified as at-risk by a physician.

In certain aspects the application relates to a method for inhibiting viral entry (e.g., HIV entry) into a cell, the method comprising contacting the cell with an effective amount of an agent selected from the group consisting of: a BD agent; a BD-inducing agent; an agent that potentiates the interaction between a BD-polypeptide and a chemokine receptor; and an agent that potentiates the interaction between a BD-polypeptide and the virus. In this context, "contacting the cell" is meant merely that the cell is placed in fluid contact with the active agent, although the agent will not necessarily bind specifically, or at all, to the cell. For example, an epithelial cell bathed in an emulsion containing an HBD polypeptide, but not bound to such polypeptide, would be considered to have been contacted with the polypeptide.

Agents described herein may be used for HIV infections as well as infections of other viruses, and particularly those that associate with the CXCR4 receptor.

The methods and compositions of the invention are useful for different subjects or patients. Examples of subjects include but are not limited to human subjects at risk for exposure to HIV or subjects who have contracted or been infected by HIV. There examples of high-risk groups were described in Kellerman et al., Journal of Acquired Immune Deficiency Syndromes (October 2002) 31:202-10. Another example of high-risk group may include any patient who is in need of blood transfusion. Subjects who have contracted or been infected by HIV already may benefit from the invention, as further HIV replication in the subjects may be inhibited by the methods and compositions described herein.

Unlike most antiviral agents, resistance to beta-defensins is rare in pathogenic organisms. Accordingly, the agents of the invention may be used in situations where use of a traditional antiviral agent would be ill-advised because of the risk of resistance development. For example, an agent of the invention may be administered to patients that are unlikely to follow a complex dosing regimen or who do not have regular access to medical professionals.

The agents of the invention may be used in combination with other antimicrobial or antiviral agent. For example, a subject patient having contracted HIV may be more susceptible to other pathogens such as candida, bacteria, or another virus. Thus, it would be desirable to use an agent of the invention to inhibit HIV replication in the subject while simultaneously preventing the subject from contracting other pathogens. An antiviral agent to be used in combination with an agent of the invention may target a portion of an HIV virus such as for example an HIV protease and an HIV reverse transcriptase.

An agent of the invention may be used in preparing a pharmaceutical package comprising labels and instruction to use. The pharmaceutical package may further comprise another antimicrobial or antiviral agent to be used in combination with an agent of the invention, as described above.

A nucleic acid encoding a BD polypeptide or BD-inducing polypeptide may be administered to a subject so as to stimulate production of the active polypeptide in vivo. For this purpose, various techniques have been developed for modification of target tissue and cells in vivo. A number of viral vectors have been developed which allow for transfection and, in some cases, integration of the virus into the host. See, for example, Dubensky et al. (1984) Proc. Natl. Acad. Sci. USA 81, 7529-7533; Kaneda et al., (1989) Science 243,375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In general, the manner of introducing the nucleic acid will depend on the nature of the tissue, the efficiency of cellular modification required, the number of opportunities to modify the particular cells, the accessibility of the tissue to the nucleic acid composition to be introduced, and the like. The DNA introduction need not result in integration. In fact, non-integration often results in transient expression of the introduced DNA, and transient expression is often sufficient or even preferred. It will typically be desirable to achieve expression of BD polypeptides and inducing polypeptides in various epithelial cell types, particularly those that do not normally express BD polypeptides at high levels. It may also be desirable to achieve expression of such polypeptides in immune cells, e.g. T cells and cells found in proximity to such cells, e.g. cells of the bone marrow, thymus and blood stream generally.

Any means for the introduction of polynucleotides into mammals, human or non-human, may be adapted to the practice of this invention for the delivery of the various constructs of the invention into the intended recipient. In one embodiment of the invention, the nucleic acid constructs are delivered to cells by transfection, i.e., by delivery of "naked" nucleic acid or in a complex with a colloidal dispersion system. A colloidal system includes macromolecule complexes, nanocapsules, microspheres, beads, and lipid-based systems including oil-in-water emulsions, micelles, mixed micelles, and liposomes. An exemplary colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

Optionally, liposomes or other colloidal dispersion systems are targeted. Targeting can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. A certain level of targeting may be achieved through the mode of administration selected.

In certain variants of the invention, the nucleic acid constructs are delivered to cells using viral vectors. The transgene may be incorporated into any of a variety of viral vectors useful in gene therapy, such as recombinant retroviruses, adenovirus, adeno-associated virus (AAV), herpes simplex derived vectors, hybrid adeno-associated/herpes simplex viral vectors, influenza viral vectors, especially those based on the influenza A virus, and alphaviruses, for example the Sinbis and semliki forest viruses, or recombinant bacterial or eukaryotic plasmids. The following additional guidance on the choice and use of viral vectors may be helpful to the practitioner. As described in greater detail below, such embodiments of the subject expression constructs are specifically contemplated for use in various in vivo and ex vivo gene therapy protocols.

A viral gene delivery system useful in the present invention utilizes adenovirus-derived vectors. Adenovirus can infect virtually all epithelial cells regardless of their cell cycle stage. In addition, adenoviral vector-mediated transfection of cells is often a transient event. A combination of immune response and promoter silencing appears to limit the time over which a transgene introduced on an adenovirus vector is expressed. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus is particularly suitable for use as a gene transfer vector because of its mid-sized genome, ease of manipulation, high titer, wide target-cell range, and high infectivity. The virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., 10.sup.9-10.sup.11 plaque-forming unit (PFU)/ml, and they are highly infective. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted polynucleotide of the invention can be under control of, for example, the E1A promoter, the major late promoter (MLP) and associated leader sequences, the viral E3 promoter, or exogenously added promoter sequences.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 d1324 or other strains of adenovirus (e.g., Ad2, Ad3, Ad7 etc.) are well known to those skilled in the art.

Adenoviruses can be cell type specific, i.e., infect only restricted types of cells and/or express a transgene only in restricted types of cells. For example, the viruses may be engineered to comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has Genbank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by restriction digest, linker ligation or filling in of ends, and ligation.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/34667 1) by Kovesdi et al.; PCT/FR94/00624 (WO94/28152) by Imler et al.;PCT/FR94/0085 1 (WO 95/02697) by Perrocaudet et al., PCT/US95/14793 (WO96/14061) by Wang et al.

Yet another viral vector system useful for delivery of the subject polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129). AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is usually about 4.4 kb (Kotin, R. M., Human Gene Therapy 5:793-801, 1994 and Flotte, et al. J. Biol. Chem. 268:3781-3790, 1993).

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J. Biol. Chem. 268: 3781-3790, 1993) or chromatographic purification, as described in O'Riordan et al., WO97/08298. Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

Hybrid Adenovirus-AAV vectors have been generated and are typically represented by an adenovirus capsid containing a nucleic acid comprising a portion of an adenovirus, and 5' and 3' inverted terminal repeat sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0-1) and includes the 5' ITR and the packaging/enhancer domain. The 3' adenovirus sequences of the hybrid virus include the right terminal 3' ITR sequence which is about 580 nucleotides (about bp 35,353-end of the adenovirus, referred to as about map units 98.4-100).

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. Integration and stable expression require the division of host cells (Paskind et al. (1975) Virology 67:242). This aspect is particularly relevant for the treatment of PVR, since these vectors allow selective targeting of cells which proliferate, i.e., selective targeting of the cells in the epiretinal membrane, since these are the only ones proliferating in eyes of PVR subjects.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a protein of the present invention, e.g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are all well known to those skilled in the art. A preferred retroviral vector is a pSR MSVtkNeo (Muller et al. (1991) Mol. Cell Biol. 11:1785 and pSR MSV(Xbal) (Sawyers et al. (1995) J. Exp. Med. 181: 307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses, including lentiviruses, have been used to introduce a variety of genes into many different cell types, including epithelial cells, lymphocytes and bone marrow cells, in vitro and/or in vivo (see for example, review by Federico (1999) Curr. Opin. Biotechnol. 10:448; Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Other viral vector systems that can be used to deliver a polynucleotide of the invention have been derived from vaccinia virus, alphavirus, poxvirus, arena virus, polio virus, and the like. Such vectors offer several attractive features for various mammalian cells. (Ridgeway (1988) In: Rodriguez R L, Denhardt D T, ed. Vectors: A survey of molecular cloning vectors and their uses. Stoneham: Butterworth; Baichwal and Sugden (1986) In: Kucherlapati R, ed. Gene transfer. New York: Plenum Press; Coupar et al. (1988) Gene, 68: 1-10; Walther and Stein (2000) Drugs 60:249-71; Timiryasova et al. (2001) J Gene Med 3:468-77; Schlesinger (2001) Expert Opin Biol Ther 1:177-91; Khromykh (2000) Curr Opin Mol Ther 2:555-69; Friedmann (1989) Science, 244:1275-1281; Ridgeway, 1988, supra; Baichwal and Sugden, 1986, supra; Coupar et al., 1988; Horwich et al. (1990) J. Virol., 64:642-650).

Toxicity and therapeutic efficacy of agents and compositions of the invention can be determined by standard pharmaceutical procedures in cell cultures or experimental animals, e.g., for determining the Ld50 (the dose lethal to 50% of the population) and the Ed50 (the dose therapeutically effective in 50% of the population). The dose ratio between toxic and therapeutic effects is the therapeutic index and it can be expressed as the ratio LD50/ED50. Agents or compositions which exhibit large therapeutic induces are preferred. While agents or compositions that exhibit toxic side effects may be used, care should be taken to design a delivery system that targets such agents or compositions to the site of affected tissue in order to minimize potential damage to uninfected cells and, thereby, reduce side effects.

The data obtained from the cell culture assays and animal studies can be used in formulating a range of dosage for use in humans. The dosage of such agents or compositions lies preferably within a range of circulating concentrations that include the ED50 with little or no toxicity. The dosage may vary within this range depending upon the dosage form employed and the route of administration utilized. For any agent or composition used in the method of the invention, the therapeutically effective dose can be estimated initially from cell culture assays. A dose may be formulated in animal models to achieve a circulating plasma concentration range that includes the IC50 (i.e., the concentration of the test agent or composition which achieves a half-maximal inhibition of symptoms) as determined in cell culture. Such information can be used to more accurately determine useful doses in humans. Levels in plasma may be measured, for example, by high performance liquid chromatography.

EXEMPLIFICATION

The invention now being generally described, it will be more readily understood by reference to the following examples, which are included merely for purposes of illustration of certain aspects and embodiments of the present invention, and are not intended to limit the invention.

For reasons poorly understood, transmission of HIV-1 through oral secretions is uncommon [Rogers et al.; Moore et al.]. Despite the ready demonstration of HIV-1 RNA, proviral DNA and infected cells in salivary secretions of infected persons [Goto, et al.; Baron et al.], infectious virus is rarely isolated from saliva [Rogers et al.; Barr et al.; Coppenhaver, et al.]. Thus, diminished infectivity of HIV-1 within oropharyngeal tissues [Herz et al.] may underlie the infrequent transmission of HIV-1 through this route. A better understanding of this apparent protection is particularly important as more than 90% of HIV-1 cases worldwide have been transmitted across other mucosal surfaces [Smith et al.].

Numerous studies have been conducted to identify the HIV inhibitory activity in saliva of healthy and infected individuals [reviewed by Shugars et al.]. Many salivary inhibitors of HIV-1 have been proposed; e.g., amylase, lactoferrin, proline-rich peptides, salivary mucins, thrombospondin, and secretory leukocyte protease inhibitor [Id.]. The importance of these agents in oral mucosal protection remains to be demonstrated. It is shown here that mRNA expression of beta-defensins can be induced in oral epithelial cells by exposure to HIV-1 and that these defensins can inhibit HIV propagation in vitro. In contrast to other mucosal body sites, where hBD-2 and -3 are induced only during inflammation [O'Neil et al.; Wehkamp et al; Bajaj-Elliott et al.; Ong et al.; Liu et al.], expression of these host defense agents is always measurable even in normal uninflamed oral epithelium [Dale et al.]. Since the reported concentration of hBD-2 in normal oral epithelium is about 10 μmoles/g tissue [Sawaki et al.], well within the inhibitory concentrations reported in the in vitro experiments with the X4 phenotype, further induction of hBD-2 (or hBD-3) by mucosal exposure to virus may provide protection against X4-tropic and potentially also against R5-tropic viruses. It should be noted that induction of hBD mRNA expression in NHOEC is accompanied by increased expression of hBD protein. (A. Weinberg et al., unpublished data).

As shown in the examples and figures herein, HIV-1 induced expression of hBD-2 and -3 mRNA in normal human oral epithelium and cells ("NHOEC") and that these defensins, but not hBD-1, inhibit HIV-1 replication in immunocompetent cells. Inhibition involves the binding of HIV-1 directly, as well as an additional downmodulation of cell surface CXCR4 expression. Inhibition of HIV-1 replication by beta-defensins may play an important role in protecting the oral cavity and other mucosal surfaces from infection; preferential inhibition of CXCR4-tropic (X4) HIV-1 strains may help to explain the selective acquisition of CCR5-tropic (R5) HIV-1 isolates after in vivo mucosal exposure.

While it is premature to speculate how beta-defensins bind HIV-1, an interaction with gp120 is plausible. Polyanionic compounds exert their anti-HIV-1 activity by binding to the positively charged sites in the V3 loop of gp120 [Schols et al.; Witvrouw et al.]. Like other polycationic peptides which block infection with X4 HIV-1 isolates (e.g., T22, T134, and ALX40-4C) [De Clercq et al.], the direct antiretroviral effect of beta-defensins might be predicted to be very different, perhaps interacting with other viral surface domains.

Example 1

Materials and Methods

Cells and Viruses

Peripheral blood mononuclear cells (PBMC) were stimulated with phytohemagglutinin (PHA) and interleukin (IL)-2 [Pauwels et al.]. MT4 and CEM X4/R5 T-cell lines, and GHOST CXCR4 and CCR5-transfected osteosarcoma cells cotransfected with the HIV-2 long terminal repeat driving expression of the green fluorescent protein (hGFP), and all viral isolates were obtained through the AIDS Research and Reference Reagent Program. Normal human oral epithelium and cells (NHOEC) were prepared as described [Krisanaprakorkit et al., 1998 and 2000]. Viral stocks were propagated in PHA-stimulated, IL-2 treated PBMC, and tissue culture dose for 50% infectivity was determined [Quinones-Mateu et al.].

Generation of Recombinant Human β-Defensins (hBDs)

Recombinant hBD-1 and -2 (rhBD-1 and -2) were produced from the infection of Sf21 cells with baculovirus constructs as described [Valore et al.]. Recombinant hBD-3 (rhBD-3) was produced using an hBD-3-His tag fusion construct, generated by PCR and cloned into pET-30c [Harder et al.]. Identity, purity and biological activity of rhBD-1, -2, and -3 were confirmed by acid urea-PAGE migration, Western analysis with native peptides, N-terminal amino acid sequencing, matrix assisted laser desorption ionization time of flight mass spectrometry, and killing of *Escherichia coli* ML35p [Valore et al.; Harder et al.].

Real-Time RT-PCR Assay to Quantify hBD mRNA

RNA was extracted from NHOEC monolayers post HIV-1 challenge [multiplicity of infection (MOI), 0.01 infectious unit/cell] using TRIzol according to the manufacturer's protocol (Invitrogen Life Technologies, Carlsbad, Calif., USA). Human keratin 5 RNA was used to normalize RNA content in each preparation. Intron spanning primers used and PCR conditions for these reactions have been described previously [Krisanaprakorkit et al., 1998 and 2000; Harder et al.]. Each 25-μl PCR mixture consisted of 125 ng RNA, primers (0.4 μM each), 0.4 mM dNTPs, 5 mM MgCl2, a mixture of reverse transcriptase and Taq DNA polymerase, 1 3 PCR buffer, RNase inhibitor (5 U), and SYBR Green dye diluted 1:2500 (Sigma, St. Louis, Mo., USA) as described [Weber et al.]. Standard curves were constructed using RNA generated by transcribing hBD-1, -2, or -3 plasmids using the RiboProbe in vitro transcription system (Promega, Madison, Wis., USA). Concentration of mRNAs was determined by spectrometry at 260 nm. Single-stock solutions of serial dilutions from 107 to 10 RNA copies were prepared and stored at −80° C. All real-time RT-PCR amplifications, data acquisition, and analysis were performed using the Smart Cycler System, software version 1.2d (Cepheid, Sunnyvale, Calif., USA).

Anti-HIV-1Activity and Cytotoxicity of hBD

HIV-1 isolates were incubated with increasing concentrations (5-40 μg/ml) of hBD-1, -2, and -3, in three different conditions: high salt complete medium (RPMI-1640 or DMEM supplemented with 10% fetal bovine serum, FBS); high salt medium in the absence of FBS; or low salt medium (10 mM phosphate buffer), 37° C. for 1 h. Respective mixtures were used to infect PBMC, Ghost X4/R5 or CEM X4/R5 cells at an MOI of 0.01 IU/ml. After 2 h incubation at 37° C., 5% CO2, cells were washed three times with phosphate-buffered saline (PBS) and cultured in complete medium for 48 h. In the case of Ghost X4/R5 cells, these were washed, resuspended in PBS, and analyzed by fluorescence microscopy for GFP expression as described [Morner et al.]. Cell-free supernatants from PBMC, Ghost X4/R5 and CEM X4/R5 cultures were used to monitor infectivity by the reverse transcriptase (RT) assay [Quinones-Mateu et al.]. The 50% inhibitory concentration (IC50) of each hBD was determined using X4 or R5 HIV-1 isolates. Viruses (0.01 MOI) were incubated with increasing concentrations of hBD-1, -2, and 3 (up to 40 g/ml) in low salt medium for 1 h and used to infect CEM X4/R5 cells. After 2 h incubation at 37° C., 5% CO2, cells were washed twice with PBS and cultured in complete medium. Supernatant samples were removed on day 5 post-infection and virus production was measured using AIDS 2003, Vol 17 No X 2 the RT assay [Id.]. Cytotoxicity of hBD was quantified by determining the number of viable cells using a tetrazolium-based colorimetric (MTT) assay [Pauwels et al.].

Flow Cytometric Analysis

Unstimulated PBMC were treated with 30 μg/ml hBD-1, -2, or -3 in high salt medium (RPMI-1640) in the absence of FBS, 3 h. The CXCR4 natural ligand SDF-1α (R&D Systems, Minneapolis, Minn., USA) and the CCR5 antagonist PSC-RANTES were used as controls. Cells were incubated with peridinin chlorophyll protein-conjugated anti-human CD4 antibody, and either phycoerythrin (PE)-conjugated anti-human CXCR4 antibody, PE-conjugated anti-human CCR5 antibody, or PE-conjugated mouse immunoglobulin G2a (IgG2a), isotype standard (PharmMingen, San Diego, Calif., USA) [Salkowitz et al.]. Fluorescence intensity was reported as receptor density by quantitative flow cytometry (FACSCaliber; Becton Dickenson, San Jose, Calif., USA) [Iyer et al.]. Data were analyzed using CELLQuest software (Becton Dickenson).

Confocal Microscopy

CEM X4/R5 cells were grown in RPMI-1640 medium containing 5% FBS and 400 μg/ml G418. Cells were collected, washed twice with PBS, resuspended in RPMI with 0.5% FBS or supplemented with 20 μg/ml recombinant hBD-2 or -3, and incubated at 37° C., 5% CO2 for 3 h. A second aliquot of cells, after incubation with hBD, was treated with FACS/Perm (PharMingen) at room temperature for 10 min and then washed three times with PBS. A third aliquot of cells was fixed in 1% paraformaldehyde on ice for 30 min, washed three times with PBS, and then incubated with 20 µg/ml hBD-2 or -3. Cells were stained with PE-labeled CXCR4 or CCR5 (PharMingen), or with primary goat anti-hBD-2 antibodies (Cell Sciences, Norwood, Mass., USA), or with rabbit anti-hBD-3 antibodies (Orbingen, San Diego, Calif., USA) at room temperature for 90 min, followed by washing three times with PBS. Fluorescein isothiocyanate-labeled rabbit anti-goat IgG (Jackson ImmunoResearch, West Grove, Pa., USA) for detection of hBD-2, or goat anti-rabbit IgG (Sigma) for detection of hBD-3, were added, respectively, at room temperature and incubated for 90 min. Cells were washed twice with PBS, resuspended in 1% paraformaldehyde (except for the pre-fixed cells), and stored at 48 C prior to analysis. All samples were observed using a dual scanning confocal microscope system (Zeiss LSM 510, Oberkochem, Germany) and analyzed with the Zeiss LSM 5 Image Browser.

Immunogold Transmission Electron Microscopy

MT4 cells in RPMI, or X4 strain B-HXB2 viral particles in 10 mM phosphate buffer (PB), were incubated with 20 µg/ml hBD-2 and -3 at 37° C. for 1 h. Cells and virions were centrifuged (15 min, 1200 rpm for cells; 30 min, 35 000 3 g for virus) and washed twice with PBS to remove unbound hBD. Cells and virions were mixed and fixed with 4% paraformaldehyde/0.5% glutaraldehyde, dehydrated, embedded in LR WHITE resin (London Resin Company Ltd, Berkshire, UK), and labeled after embedding as described [Briquet et al.]. Ultrathin sections were incubated with primary rabbit anti-hBD-2 or anti-hBD-3 antibody (1:100 dilution) overnight at 48 C, washed, and incubated for 2 h at room temperature with a 1:10 dilution of goat anti-rabbit IgG conjugated with 10 nm gold particles (Ted Pella Inc., Redding, Calif., USA) as the second antibody. Negative controls included HIV-infected cells incubated with both hBD and only the secondary gold-conjugated antibody, or HIV-infected cells incubated with primary and secondary antibodies in the absence of hBD. Embedding and preparation for conventional transmission electron microscopy were performed as described [Id.].

Example 2

HIV-1 Induces hBD-2 and hBD-3 but not hBD-1 mRNA in NHOEC

Figure 1:
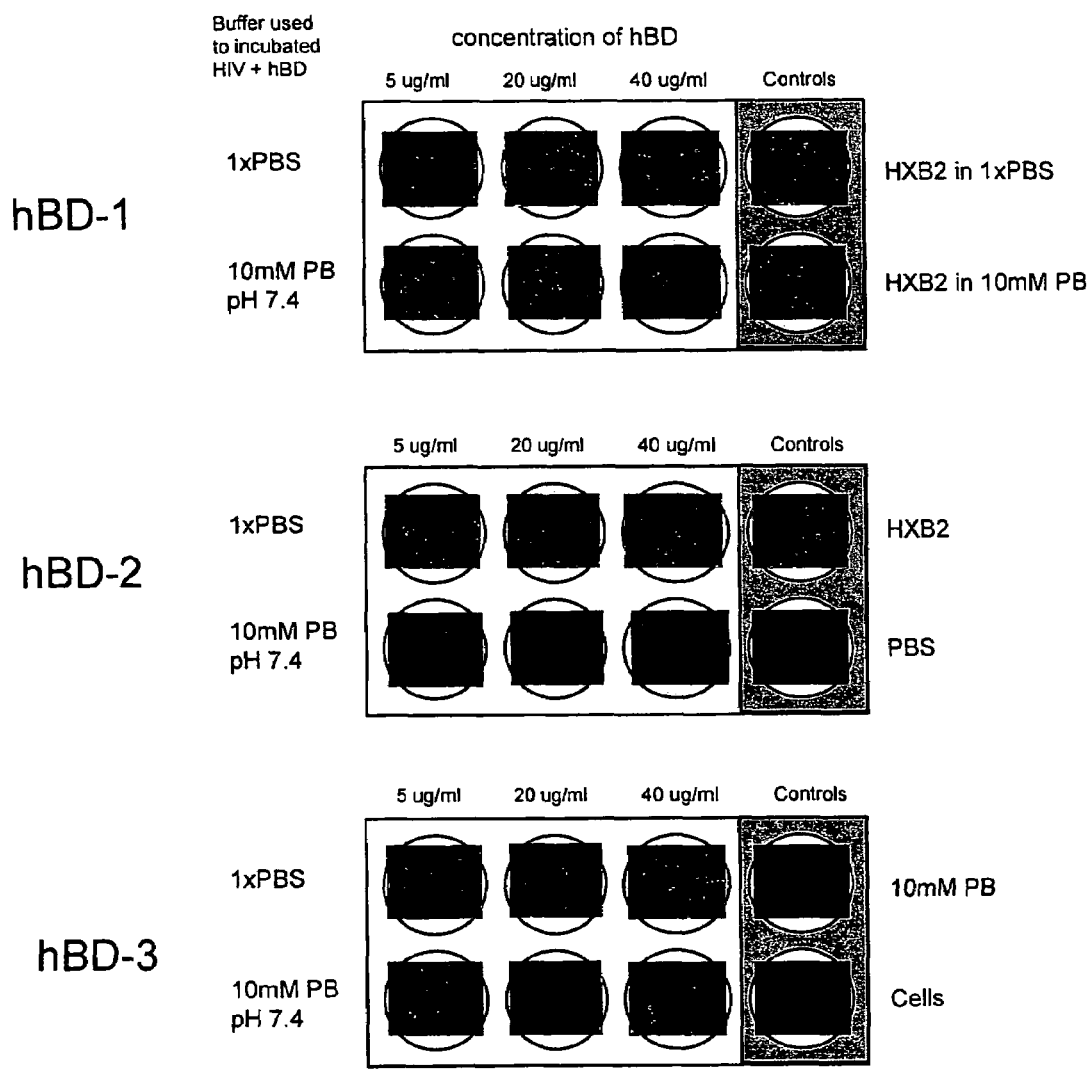
FIG. 1 shows the effects of human beta-defensin-1, -2 and -3 on the infection of ghost CD4/CCR5/CXCR5 cells by X4-type green fluorescent protein reporter HIV.
Figure 2:
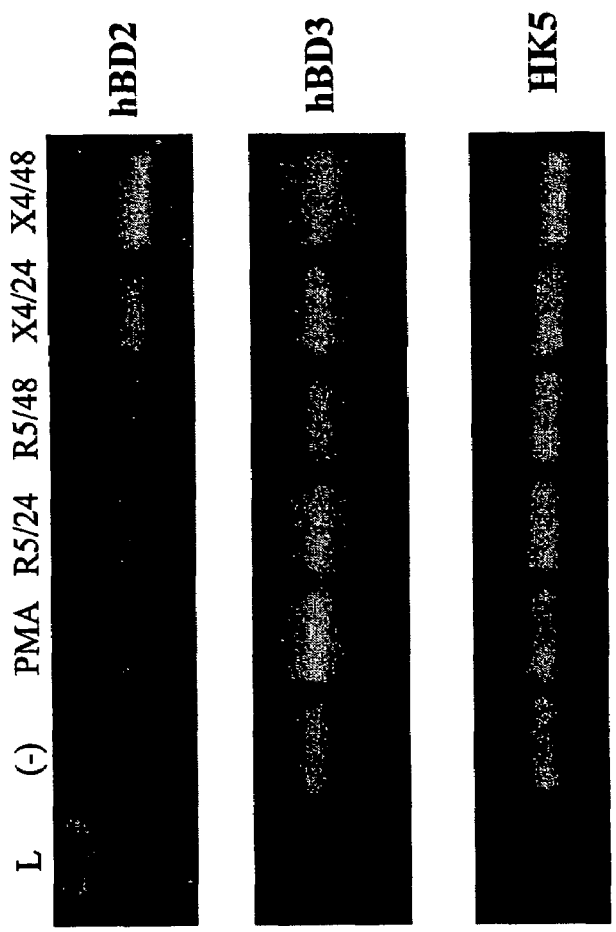
FIG. 2 shows the effect of HIV on the expression of HBD-2 and HBD-3 transcripts.
Figure 3:
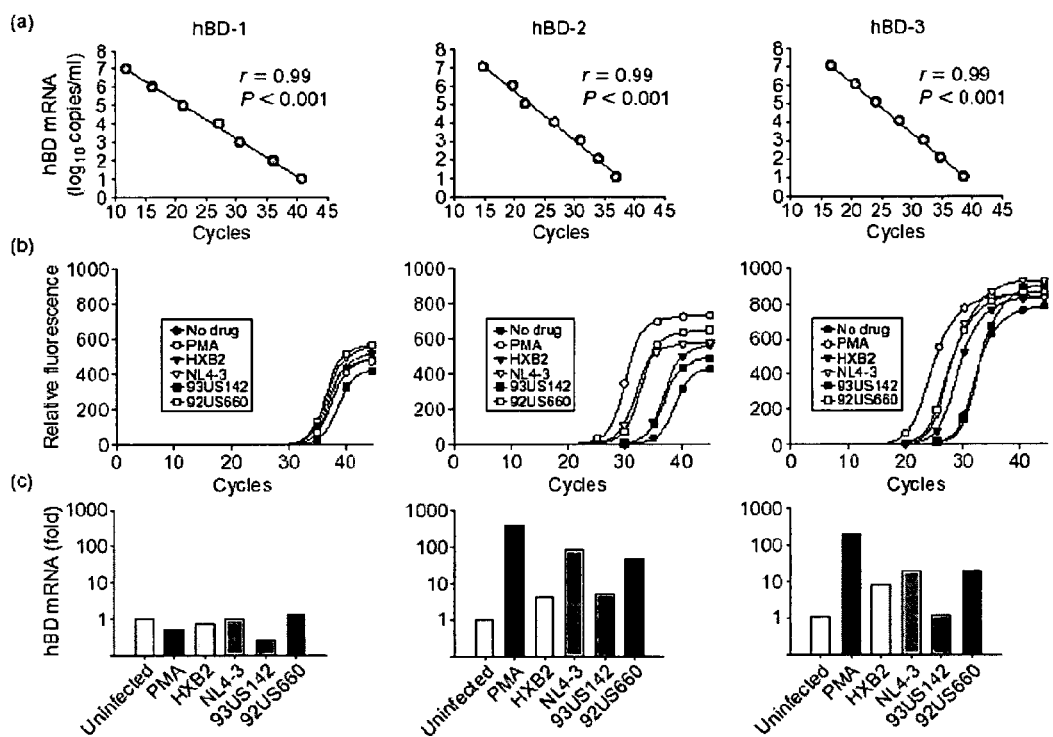
FIG. 3 shows HIV-1-induced expression of hBD-2 and -3. NHOEC monolayers were exposed to X4 HIV-1 strains B-HXB2 and B-NL4-3 or R5 strains B-93US142 and B-92US660 at an MOI of 0.01 infectious unit/cell. After 48 h, hBD-1, -2, and -3 mRNA expression was determined by real-time PCR. (a) Standard curves generated using the relationship of known number of input templates to the cycle threshold (i.e., PCR cycle number at which the mean fluorescence increases to 10 SD above baseline). Cycle threshold is directly proportional to the log of the input copy equivalents. Linear dynamic ranges and regression values are indicated. (b) Quantification of hBD mRNA in the presence and absence of HIV-1. (c) Comparison of hBD expression relative to the uninfected culture. PMA, phorbol myristate acetate, positive control. Results are representative of three independent experiments.

NHOEC monolayers were challenged with four different HIV-1 strains representing both viral bio-phenotypes (i.e., SI/X4, B-HXB2 and B-NL4-3; NSI/R5, B-93US142 and B-92US660) Forty-eight hours postinfection, hBD-1, -2, and -3 mRNA expression was measured by real-time PCR. All HIV-1 strains induced hBD-2 and hBD-3 mRNA 4- to 78-fold above baseline (FIG. 3). No induction of hBD-1 mRNA was observed. Supernatants from uninfected MT4 cells or PBMC, used to grow respective viral strains, did not induce either hBD-2 or -3 mRNA expression (data not shown). HBD-2 and -3 transcript expression increased with viral exposure time and was maintained as long as 72 h post-exposure (data not shown). Finally, although HIV-1 can infect epithelial cells from other mucosal surfaces [Yahi. et al.; Fotopoulos et al.], analyses of viral RT activity in culture supernatant [Quinones-Mateu et al.] and real-time PCR to detect proviral DNA in cells failed to detect infection of NHOEC by HIV-1 (data not shown).

Example 3

HBD-2 and hBD-3 Inhibit HIV-1 Replication

Figure 4:
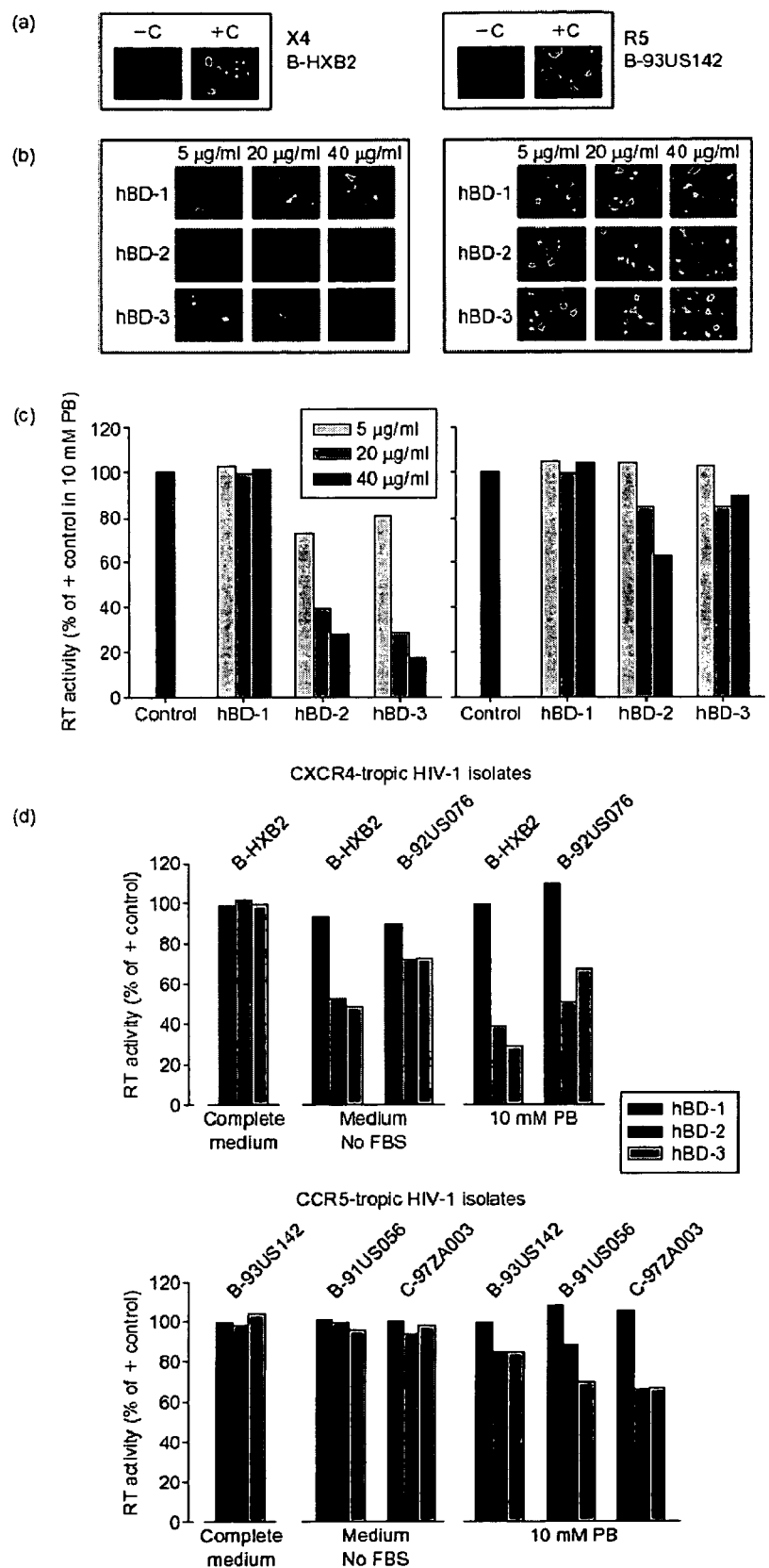
FIG. 4 shows anti-HIV-1 activity of hBD. HIV-1 strains (X4 HXB2 and R5 93US142) were incubated in 10 mM PB with increasing concentrations of hBD and used to infect GHOST X4/R5 cells. (a) Qualitative determination of HIV-1 infection, measured by GFP fluorescence, in the absence (−C) and presence (+C) of virus preincubated in 10 mM PB. (b)

Since the antibacterial activity of beta-defensins is sensitive to high salt and serum concentrations, the anti-HIV-1 activity of hBD was initially evaluated in a low salt, serum free environment, mimicking oral mucosal conditions [Mandel et al.]. Two HIV-1 isolates (X4 B-HXB2 and R5 B-93US142) were preincubated for 1 h with increasing concentrations of recombinant hBD-1, -2, and -3, in 10 mM phosphate buffer (PB). GHOST CCR5/CXCR4 cells were then exposed to the mixtures for 48 h in complete medium. While hBD-1 had no effect, preincubation of HIV-1 with either hBD-2 or hBD-3 in 10 mM PB showed anti-HIV-1 activity (FIG. 4b), which was concentration dependent and greater against the X4 B-HXB2 strain than against the R5 B-93US142 isolate (61% versus 15% inhibition with 20 µg/ml hBD-2, respectively) (FIG. 4c). When CXCR4- and CCR5-tropic HIV-1 strains were preincubated with beta-defensins in high salt medium (DMEM) supplemented with 10% FBS, no antiviral effect was detected (FIG. 4d). However, preincubation in DMEM without FBS inhibited replication of X4, but not R5, HIV-1 isolates (FIG. 4d). Under low salt conditions (i.e., 10 mM PB, no FBS) the 50% inhibitory concentration for both agents against X4 and R5 viruses ranged from 9 to 19 µg/ml and 20 to 40 µg/ml, respectively. These findings suggest that hBD-2 and -3 may have a direct electrostatic interaction with HIV-1 particles that inhibits infection. In addition, the greater activity against X4 HIV-1 strains suggested either an electrostatic preference for X4 versus R5 binding or a selective effect on the viral co-receptor.

Example 4

HBDs are not Toxic to Human Cells

A thiazolyl blue-based colorimetric assay (MTT method) [Pauwels et al.] revealed no cytotoxicity against PBMC, CEM X4/R5, MT4 or GHOST X4/R5 cells using up to 40 µg/ml of each hBD, in the presence or absence of serum.

Example 5

HBD-2 and -3 Downmodulate CXCR4, but not CCR5

The more effective inhibition of X4 HIV-1 strains over R5 HIV-1 isolates (FIG. 4), led us to ask whether hBD-2 and -3 interact with the HIV co-receptor CXCR4. Flow cytometric analysis of hBD-1, -2 or -3 preincubated PBMC showed that CCR5 expression was not altered by hBD (FIG. 5). Incubation with hBD-1 did not affect surface expression of CXCR4. Surface expression of CXCR4 was decreased by 51%±18% and 52%±20% (SD) respectively after incubation with 30 µg/ml of hBD-2 or hBD-3 (FIG. 5). Similar results were obtained with CEM cells expressing CXCR4 and CCR5.

To explore the mechanism of this effect, CEM X4/R5 cells were incubated with hBD-2 and -3 and then examined for surface expression of CXCR4 and CCR5 by confocal microscopy. This exposure dramatically decreased surface expression of CXCR4 (but not CCR5). Subsequent labeling with polyclonal antibodies against hBD-2 or hBD-3 failed to detect these peptides on the cell surface. Since chemokine receptors may internalize after ligation, CEM X4/R5 cells were first fixed with paraformaldehyde, then incubated with hBD-2 and finally labeled with anti-hBD-2 antibody. This time, hBD-2 was found bound to the cell membrane. Finally, to visualize hBD-2 internalization, live CEM X4/R5 cells were incubated first with hBD-2, then permeabilized and incubated with anti-hBD-2 antibodies. HBD-2 was identified by confocal microscopy with a staining pattern suggestive of internalization. Similar results were observed when CEM X4/R5 cells were treated with hBD-3. Collectively, these results suggest that both hBD-2 and -3 bind to cell surface CXCR4 and induce internalization of the bound complex.

Example 6

HBD-2 and -3 Interact with Both HIV-1 and the Host Cell

In order to verify a direct hBD-virion interaction, the X4 B-HXB2 and R5-C-97ZA003 HIV-1 strains was incubated with 20 μg/ml of each hBD in 10 mM PB for 1 h, followed by pelleting and extensive washing. Virions were then used to infect GHOST X4/R5 cells. The anti-HIV-1 effect of hBD-2 and -3 was maintained after washing, suggesting a direct and irreversible effect on the virion. Moreover, subsequent addition of hBD-2 or hBD-3 to the cell-virus mixture enhanced anti-HIV-1 activity only against the CXCR4-tropic BHXB2 strain (FIG. 6a). Taken together, these data suggest that the inducible defensins have both a direct inhibitory effect on HIV-1 infectiousness and an additional antiviral effect that is probably mediated through downmodulation of CXCR4. To further define these interactions, MT4 cells, infected with the CXCR4 tropic B-HXB2, were incubated with hBD-2 or -3 in RPMI, followed by the addition of anti-hBD-2 or -3 antibodies and goat anti-rabbit IgG conjugated with 10-nm gold particles. Gold particles were observed bound both to virions and to the MT4 cellular membrane in samples incubated with hBD-2 or -3 (FIG. 6b), but not in samples incubated in the absence of hBD. Taken together, these results indicate that hBD-2 and -3 bind directly to virions inducing irreversible inhibition of HIV replication and also bind to host cells inducing downmodulation of the CXCR4 chemokine coreceptor.

References

1. Krisanaprakornkit S, Weinberg A, Perez C N, Dale B A. Expression of the peptide antibiotic human beta-defensin 1 in cultured gingival epithelial cells and gingival tissue. Infect Immun 1998, 66:4222-4228.
2. Krisanaprakornkit S, Kimball J R, Weinberg A, Darveau R P, Bainbridge B W, Dale B A. Inducible expression of human betadefensin 2 by Fusobacterium nucleatum in oral epithelial cells: multiple signaling pathways and role of commensal bacteria in innate immunity and the epithelial barrier. Infect Immun 2000, 68:2907-2915.
3. Pauwels R, Balzarini J, Baba M, et al. Rapid and automated tetrazolium-based colorimetric assay for the detection of anti-HIV compounds. J Virological Methods 1988, 20:309-321.
4. Quinones-Mateu M E, Ball S C, Marozsan A J, et al. A dual infection/competition assay shows a correlation between ex vivo human immunodeciency virus type 1 .tness and disease progression. J Virol 2000, 74:9222-9233.
5. Valore E V, Park C H, Quayle A J, Wiles K R, McCray P B, Jr., Ganz T. Human beta-defensin-1: an antimicrobial peptide of urogenital tissues. J Clin Invest 1998, 101:1633-1642.
6. Harder J, Bartels J, Christophers E, Schroder J M. Isolation and characterization of human beta -defensin-3, a novel human inducible peptide antibiotic. J Biol Chem 2001, 276:5707-5713.
7. Weber J, Rangel H R, Chakraborty B, et al. A novel TaqMan realtime PCR assay to estimate ex vivo human immunodeficiency β-defensins 2 and 3 inhibit HIV-1 Quinones-Mateu et al. 9 virus type 1 fitness in the era of multi-target (pol and env) antiretroviral therapy. J Gen Virol 2003, 84:2217-2228.
8. Momer A, Bjorndal A, Albert J, et al. Primary human immunodeficiency virus type 2 (HIV-2) isolates, like HIV-1 isolates, frequently use CCR5 but show promiscuity in coreceptor usage. J Virol 1999, 73:2343-2349.
9. Salkowitz J R, Purvis S F, Meyerson H, et al. Characterization of high-risk HIV-1 seronegative hemophiliacs. Clin Immunol 2001, 98:200-211.
10. Iyer S B, Hultin L E, Zawadzki J A, Davis K A, Giorgi J V. Quantitation of CD38 expression using QuantiBRITE beads. Cytometry 1998, 33:206-212.
11. Briquet S, Vaquero C. Immunolocalization studies of an antisense protein in HIV-1-infected cells and viral particles. Virology 2002, 292:177-184.
12. Yahi N, Baghdiguian S, Moreau H, Fantini J. Galactosyl ceramide (or a closely related molecule) is the receptor for human immunodeficiency virus type 1 on human colon epithelial HT29 cells. J Virol 1992, 66:4848-4854.
13. Fotopoulos G, Harari A, Michetti P, Trono D, Pantaleo G, Kraehenbuhl J P. Transepithelial transport of HIV-1 by M cells is receptor-mediated. Proc Natl Acad Sci USA 2002, 99:9410-9414.
14. Mandel I D. Saliva. St. Louis: C.V. Mosby Co, 1972.
15. Rogers M F, White C R, Sanders R, et al. Lack of transmission of human immunodeficiency virus from infected children to their household contacts. Pediatrics 1990, 85:210-214.
16. Moore B E, Flaitz C M, Coppenhaver D H, Nichols M, Kalmaz G D, Bessman J D, et al. HIV recovery from saliva before and after dental treatment: inhibitors may have critical role in viral inactivation. J Am Dental Assoc 1993, 124:67-74.
17. Goto Y, Yeh C K, Notkins A L, Prabhakar B S. Detection of proviral sequences in saliva of patients infected with human immunodeficiency virus type 1. AIDS Res Hum Retroviruses 1991, 7:343-347.
18. Baron S, Poast J, Cloyd M W. Why is HIV rarely transmitted by oral secretions? Saliva can disrupt orally shed, infected leukocytes. Arch Intern Med 1999, 159:303-310.
19. Barr C E, Miller L K, Lopez M R, et al. Recovery of infectious HIV-1 from whole saliva. J Am Dental Assoc 1992, 123:36-37.
20. Coppenhaver D H, Sriyuktasuth-Woo P, Baron S, Barr C E, Qureshi M N. Correlation of nonspeci.c antiviral activity with the ability to isolate infectious HIV-1 from saliva. New Engl J Med 1994, 330:1314-1315.
21. Herz A M, Robertson M N, Lynch J B, Schmidt A, Rabin M, Sherbert C, et al. Viral dynamics of early HIV infection in neonatal macaques after oral exposure to HIV-2287: an animal model with implications for maternal-neonatal HIV transmission. J Med Primatol 2002, 31:29-39.
22. Smith P D, Li L, Meng G. Mucosal events in the pathogenesis of human immunodeficiency virus type 1 infection. J Infect Dis 1999, 179 Suppl 3:S436-440.
23. Shugars D C, Wahl S M. The role of the oral environment in HIV-1 transmission. J Am Dental Assoc 1998, 129:851-858.
24. O'Neil D A, Porter E M, Elewaut D, et al. Expression and regulation of the human beta-defensins hBD-1 and hBD-2 in intestinal epithelium. J Immunol 1999, 163:6718-6724.
25. Wehkamp J, Fellermann K, Herrlinger K R, et al. Human betadefensin 2 but not beta-defensin 1 is expressed preferentially in colonic mucosa of in.ammatory bowel disease. Eur J Gastroenterol Hepatol 2002, 14:745-752.
26. Bajaj-Elliott M, Fedeli P, Smith G V, Domizio P, Maher L, Ali R S, et al. Modulation of host antimicrobial peptide (beta-defensins 1 and 2) expression during gastritis. Gut 2002, 51:356-361.
27. Ong P Y, Ohtake T, Brandt C, Strickland I, Boguniewicz M, Ganz T, et al. Endogenous antimicrobial peptides and skin infections in atopic dermatitis. [see comments] New Engl J Med 2002, 347:1151-1160.
28. Liu L, Wang L, Jia H P, Zhao C, Heng H H Q, Schutte B C, et al. Structure and mapping of the human beta-defensin HBD-2 gene and its expression at sites of in.ammation. Gene 1998, 222:237-244.
29. Dale B A, Kimball J R, Krisanaprakornkit S, Roberts F, Robinovitch M, O'Neal R, Localized antimicrobial peptide expression in human gingiva. J Periodontal Res 2001, 36:285-294.
30. Sawaki K, Mizukawa N, Yamaai T, Yoshimoto T, Nakano M, Sugahara T. High concentration of beta-defensin-2 in oral squamous cell carcinoma. Anticancer Res 2002, 22:2103-2107.
31. Schols D, Pauwels R, Desmyter J, De Clercq E. Dextran sulfate and other polyanionic anti-HIV compounds specifically interact with the viral gp 120 glycoprotein expressed by T-cells persistently infected with HIV-1. Virology 1990, 175:556-561.
32. Witvrouw M, Este J A, Quinones-Mateu M E, Reymen D, Andrei G, Snoeck R, et al. Activity of a sulfated polysaccharide extracted from the red seaweed Aghardhiella tenera against human immunodificiency virus and other enveloped viruses. Antiviral Chem Chemother 1994, 5:297-303.
33. De Clercq E. New developments in anti-HIV chemotherapy. Biochim Biophys Acta 2002, 1587:258-275.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A composition having antiviral activity, said composition comprising a pharmaceutically acceptable carrier and a Beta Defensin (BD)-inducing agent, wherein the BD-inducing agent is a polypeptide comprising the amino acid sequence of SEQ. ID. NO. 9.

2. The composition of claim 1, wherein said carrier is suitable for systemic administration.

3. The composition of claim 1, wherein said carrier is suitable for local administration.

4. The composition of claim 3, wherein said carrier is suitable for local administration to a mucous membrane.

5. A kit comprising the composition of claim 1 and an additional antiviral agent.

6. The kit of claim 5, wherein said antiviral agent targets a portion of the HIV virus selected from the group consisting of: an HIV protease and an HIV reverse transcriptase.

7. The composition of claim 1, wherein the composition is in a form selected from the group consisting of: a mouthwash, a toothpaste, an aerosol, a rectal suppository, vaginal suppository, a rectal cream, vaginal cream, a rectal film, vaginal film, a skin lotion, a condom, an eye drop, and an eye ointment.

* * * * *